(12) United States Patent
Brassil et al.

(10) Patent No.: US 10,176,887 B1
(45) Date of Patent: Jan. 8, 2019

(54) EX VIVO METHODS FOR DRUG DISCOVERY, DEVELOPMENT AND TESTING

(75) Inventors: John Brassil, Northbrook, IL (US); Christopher G. Curtis, Cardiff (GB); David Kravitz, South Barrington, IL (US)

(73) Assignee: ORGAN RECOVERY SYSTEMS, INC., Des Plaines, IL (US)

( * ) Notice: Subject to any disclaimer, the term of this patent is extended or adjusted under 35 U.S.C. 154(b) by 1697 days.

(21) Appl. No.: 11/598,800

(22) Filed: Nov. 14, 2006

Related U.S. Application Data

(60) Provisional application No. 60/736,495, filed on Nov. 14, 2005, provisional application No. 60/762,180, filed on Jan. 24, 2006.

(51) Int. Cl.
G16H 10/20 (2018.01)

(52) U.S. Cl.
CPC .................. G16H 10/20 (2018.01)

(58) Field of Classification Search
CPC ....................................... G16H 10/20
See application file for complete search history.

(56) References Cited

U.S. PATENT DOCUMENTS

| | | | |
|---|---|---|---|
| 3,877,843 A | 4/1975 | Fischel | |
| 4,618,586 A | 10/1986 | Walker | |
| 4,629,686 A | 12/1986 | Gruenberg | |
| 4,666,425 A | 5/1987 | Fleming | |
| 5,051,352 A | 9/1991 | Martindale et al. | |
| 5,066,578 A * | 11/1991 | Wikman-Coffelt | A01N 1/0226 |
| | | | 435/1.2 |
| 5,217,860 A | 6/1993 | Fahy et al. | |
| 5,328,821 A | 7/1994 | Fisher et al. | |
| 5,338,662 A | 8/1994 | Sadri | |
| 5,494,822 A | 2/1996 | Sadri | |
| 5,622,429 A | 4/1997 | Heinze | |
| 5,989,918 A | 11/1999 | Dietz et al. | |
| 6,023,630 A | 2/2000 | Bacchi et al. | |
| 6,024,698 A | 2/2000 | Brasile | |
| 6,046,046 A | 4/2000 | Hassanein | |
| 6,197,575 B1 | 3/2001 | Griffith et al. | |
| 6,582,953 B2 | 6/2003 | Brasile | |
| 6,592,567 B1 | 7/2003 | Levin et al. | |
| 6,673,594 B1 | 1/2004 | Owen et al. | |
| 6,699,231 B1 | 3/2004 | Sterman et al. | |
| 6,953,655 B1 | 10/2005 | Hassanein et al. | |
| 7,410,474 B1 | 8/2008 | Friend et al. | |
| 2002/0081750 A1* | 6/2002 | Ernest | G06Q 10/00 |
| | | | 436/518 |
| 2002/0123141 A1* | 9/2002 | Hariri | 435/366 |
| 2004/0002891 A1* | 1/2004 | Chen et al. | 705/10 |
| 2004/0038193 A1 | 2/2004 | Brasile | |
| 2004/0224298 A1 | 11/2004 | Brassil et al. | |
| 2005/0015278 A1* | 1/2005 | Ghouri | 705/2 |
| 2005/0255458 A1* | 11/2005 | Polansky | G01N 33/5308 |
| | | | 435/5 |
| 2005/0276792 A1* | 12/2005 | Kaminski et al. | 424/93.7 |
| 2006/0019326 A1 | 1/2006 | Vacanti et al. | |
| 2006/0029609 A1* | 2/2006 | Zankel | A61K 47/48246 |
| | | | 424/178.1 |
| 2007/0072222 A1 | 3/2007 | Boess et al. | |

FOREIGN PATENT DOCUMENTS

| | | |
|---|---|---|
| EP | 1 208 748 A1 | 8/2000 |
| JP | 2-258701 | 10/1990 |
| WO | WO 88/05261 A1 | 7/1988 |
| WO | WO 94/06292 | 3/1994 |
| WO | WO 95/31897 | 11/1995 |
| WO | WO 96/31779 | 10/1996 |
| WO | WO 98/09166 | 3/1998 |
| WO | WO 99/35245 | 7/1999 |
| WO | WO 99/45982 | 9/1999 |
| WO | WO 00/18226 | 4/2000 |
| WO | WO 02/026034 A2 | 4/2002 |
| WO | WO 2005/074681 A2 | 8/2005 |

OTHER PUBLICATIONS

Roediger W.E.W. et al. Effect of short-chain fatty acid on sodium absorption in isolated human colon perfused through the vascular bed. Digestive Diseases and sciences, Feb. 1981, vol. 26, No. 2, pp. 100-106.*
U.S. Appl. No. 11/802,059, filed May 18, 2007, Curtis et al.
U.S. Appl. No. 11/802,064, filed May 18, 2007, Curtis et al.
"Human Data Before Human-Trials Improving Drug Discovery and Development Productivity with Ex Vivo Metrics," Katzenbach Partners LLC, 2005, pp. 1-22.
"Perfusion of the isolated rat liver," Curtis, C.G. et al., Proceedings of the Physiological Society, Dec. 1970, pp. 14P-15P.
"Degradation of [$^3$H]Chondroitin 4-Sulphate and Re-utilization of the [$^3$H]Hexosamine Component by the Isolated Perfused Rat Liver," Macnicholl, Alan D. et al., Biochem. J. (1980), vol. 186, pp. 279-286.
"Utilization by the Isolated Perfused Rat Liver of N-Acetyl-D[1-$^{14}$C]galactosamine and N-[$^3$H]Acetyl D-galactosamine for the Biosynthesis of Glycoproteins," MacNicoll, Alan D. et al., Biochem. J.. (1978) vol. 174, pp. 421-426.
"NMR study of the whole rat bile: the biliary excretion of 4-cyano-N, N-dimethyl aniline by an isolated perfused rat live and a liver in situ," Ryan, David A. et al., Journal of Pharmaceutical & Biomedical Analysis, 1995, vol. 13, No. 6, pp. 735-745.
"Liver as major organ of phenol detoxication?," Powell, G. et al., Nature, Nov. 15, 1974, vol. 252, pp. 234-235.
"Oxidation of Sodium Sulphide by Rat Liver, Lungs and Kidney," Bartholomew, Terrence C. et al., Biochemical Pharmacology, 1980, vol. 29, pp. 2431-2437.
"The metabolic sulphation of polyethyleneglycols by isolated perfused rat and guinea-pig livers", Roy, A. B. and Maggs, J. et al., Xenobiotica, 1987, vol. 17, No. 6, pp. 725-732.

(Continued)

Primary Examiner — John A Pauls
(74) Attorney, Agent, or Firm — Oliff PLC

(57) ABSTRACT

Methods for assaying properties in tissues or organs of drugs and other chemical compounds and substances include ex vivo normothermic perfusion with a fluid containing a test substance to obtain data regarding the tissue or organ, the substance and/or an interaction of the substance and the tissue or organ. The data can be used as, for example, part of a submission to a government regulatory organization.

28 Claims, No Drawings

(56) References Cited

OTHER PUBLICATIONS

"Octan-2-sulphate degradation in the isolated perfused rat liver", Maggs, J. et al., *Biochemical Pharmacology*, 1984, vol. 33, No. 5, pp. 827-829.

*Isolated Perfused Liver Technology for Studying Metabolic and Toxicological Problems*, Powell, G.M. et al., 1989, vol. 7, No. 1, pp. 53-86.

"Organ Perfusion and Mass Spectrometry: A Timely Merger for Drug Development," Curtis, C. Gerald et al., *Current Topics in Medicinal Chemistry*, 2002, vol. 2, pp. 77-86.

*The Use of Isolated Perfused Organs*, Curtis, C. G. et al., pp. 295-302.

"Predictive Models for Tissue Metabolism-Screening Using Organ Perfusion Methods," Curtis, G., CPSA Digest 2001, http://www.milestonedevelopment.com/CPSA/2001/day3oa3.html.

"Alterations of the renal function in the isolated perfused rat kidney system after in vivo and in vitro application of S-(1,2-dichlorovinyl)-L-cysteine and S-(2,2-dichlorovinyl)-L-cysteine," Ilinskaja, O. and Vamvakas, S., Arch Toxicol (1996), vol. 70, pp. 224-229.

A New Paradigm in Perfusion, http://res-del.com/resources/AQIX_RS-I.pdf.

"The Rate of Induction of Hypothermic Arrest Determines the Outcome in a Swine Model of Lethal Hemorrhage," Alam, H. et al., *The Journal of TRAUMA Injury, Infection, and Critical Care*, Nov. 2004, vol. 57, No. 5, pp. 961-969.

"Machine Perfusion of Isolated Kidney at 37° C. Using Pyridoxalated Hemoglobin-Polyoxyethlene (PHP) Solution, UW Solution and Its Combination", T. Horiuchi et al., *Biomaterials, Art. Cells & Immob. Biotech*, vol. 20, Nos. 2-4, pp. 549-555, 1992.

"In Situ Cadaver Kidney Perfusion", Robert T. Schweizer et al., *Transplantation*, vol. 32, No. 6, pp. 482-484, Dec. 1981.

"Intermediate Normothermic Perfusion During Cold Storage of Ischemically Injured Kidneys", J.G. Maessen et al., *Transplantation Proceedings*, vol. 21, No. 1, pp. 1252-1253, Feb. 1989.

"Perfusion of Rabbit Kidneys With Glycerol Solutions at 5° C.", D.E. Pegg et al., *Cryobiology*, vol. 14, pp. 168-178, 1977.

"Seleno-DL-Methionine Reduces Freezing Injury in Hearts Protected With Ethanediol", W.J. Armitage et al., *Cryobiology*, vol. 18, pp. 370-377, 1981.

"Banking of Cells, Tissues, and Organs at Low Temperatures", David E. Pegg, *Current Trends in Cryobiology*, Plenum Press, NY, pp. 153-180, 1970.

"Effect of Pharmacologic Agents on the Function of the Hypothermically Preserved Dog Kidney During Normothermic Reperfusion", Rutger J. Ploeg et al., *Surgery*, vol. 103, No. 6, pp. 676-682, Jun. 1988.

"Is Normothermic Preservation an Alternative to Hypothermic Preservation?", R. N. Dunn et al., *Organ Preservation Basic and Applied Aspects*, Chapter 38, pp. 273-277, 1982.

"Free Radicals and Myocardial Ischemia and Reperfusion Injury", Paul J. Simpson et al., *J Lab Cin Med.*, pp. 13-30, Jul. 1987.

M.R. Buhl et al, "The Postanoxic Regeneration of 5'-Adenine Nucleotides in Rabbit Kidney Tissue during In Vitro Perfusion," 1976, pp. 175-181.

"Organko Servierungsmachine OKM 82", Von Dietmer Scholz et al., East German Article, 1983.

"MOX®-100 Renal Preservation System", Waters Instruments Medical Group, pp. 2-7, 1982.

"Organ Perfusion Systems: An Evaluation Criteria", Fereydoon Sadri, Ph.D., *T.O.P.S. Medical Corporation*, pp. 1-8, 1987.

Mar. 28, 2013 Chinese Office Action issued in Chinese Patent Application No. 200880024743.5 (with translation).

Jan. 29, 2010 Election of Species Requirement issued in U.S. Appl. No. 11/802,064.

Mar. 17, 2010 Office Action issued in U.S. Appl. No. 10/845,154.

Nov. 24, 2009 International Preliminary Report on Patentability issued in International Patent Application No. PCT/US2008/006369.

Nov. 12, 2010 Office Action issued in U.S. Appl. No. 11/802,059.

Jul. 29, 2010 Election of Species Requirement issued in U.S. Appl. No. 11/802,059.

May 16, 2011 Office Action issued in U.S. Appl. No. 10/845,154.

Apr. 1, 2009 Office Action issued in U.S. Appl. No. 10/845,154.

Nov. 1, 2007 Office Action issued in U.S. Appl. No. 10/845,154.

Feb. 8, 2007 Office Action issued in U.S. Appl. No. 10/845,154.

Aug. 6, 2008 Office Action issued in U.S. Appl. No. 10/845,154.

U.S. Appl. No. 10/845,154, filed May 14, 2004 to Brassil et al.

Sep. 6, 2011 European Office Action issued in EP 05 817 022.6.

Jan. 10, 2011 Final Office Action issued in U.S. Appl. No. 11/802,064.

Jul. 22, 2010 Office Action issued in U.S. Appl. No. 11/802,064.

Jul. 29, 2008 International Search Report issued in PCT/US2008/006368.

Feb. 28, 2006 international Search Report issued in PCT/US2005/016057.

Oct. 18, 2011 United Kingdom Office Action issued in GB0921349.7.

Oct. 18, 2011 United Kingdom Office Action issued in GB0921330.7.

Dec. 5, 2011 Office Action issued in U.S. Appl. No. 10/845,154.

Dec. 7, 2011 Office Action issued in U.S. Appl. No. 11/802,064.

Dec. 7, 2011 Office Action issued in U.S. Appl. No. 11/802,059.

Tuberose.com—Environmental Toxicity, published online Feb. 4, 2005 on the web at http://tuberose.com/Environmental_Toxicity.html, pp. 1-8.

Malgorzata Tokarska-Schlattner, et al., "Acute toxicity of doxorubicin on isolated perfused heart: response of kinases regulating energy supply," Am J Physiol Heart Circ Physiol, vol. 289, pp. H37-H47, Mar. 11, 2005.

Bell Jr. R.H. et al., "Ex-vivo isolated perfusion of the pancreas in the Syrian golden hamster," International Journal of Pancreatology, I (1986), pp. 71-81.

Takahashi H. et al., "The Use of a Perfluorochemical Emulsion as a Vascular Perfusate in Drug Absorption", Journal of Pharmacy and Pharmacology, Pharmaceutical Press, vol. 40, No. 3, Apr. 1, 1988, pp. 252-257, XP002051273.

Svensson, U.S.H. et al., "High in situ rat intestinal permeability of artemisinin unaffected by multiple dosing and with no evidence of p-glycoprotein involvement," Drug Metabolism and Disposition, 1999, vol. 27, No. 2, pp. 227-232.

D.K. Hansen et al., "Pharmacokinetic and Metabolism Studies Using Microdialysis Sampling," J. Pharmaceutical. Sciences, Jan. 1999 (Jan. 1999), vol. 88, No. 1, pp. 14-27.

G. Nowak et al., "Metabolic Changes in the Liver Graft Monitored Continuously With Microdialysis During Liver Transplantation in a Pig Model," Liver Transplantation, May 2002, vol. 8, No. 5, pp. 424-432.

S.C. Baicu et al., "Interstitial Fluid Analysis for Assessment of Organ Function," Clin. Transplant, Jun. 24, 2004, vol. 18, No. 12, pp. 16-21.

Sep. 26, 2013 Office Action issued in Chinese Patent Application No. 2013092300947840 (with translation).

May 22, 2012 Office Action issued in U.S. Appl. No. 11/802,064.

May 21, 2012 Office Action issued in U.S. Appl. No. 11/802,059.

Apr. 26, 2011 Final Office Action issued in U.S. Appl. No. 11/802,059.

Desai T.R. et al. Defining the critical limit of oxygen extraction in the human small intestine, Journal of Vascular Surgery, 1996, vol. 23, No. 5, pp. 832-838.

Coleman R.A. et al. Use of human tissue in ADME and safety profiling of development candidates, Drug Discovery Today (DDT), Nov. 2001, vol. 6, No. 21, pp. 1116-1126.

Feb. 10, 2011 European Search Report issued in GB0921330.7.

Mar. 25, 2011 European Search Report issued in GB0921349.7.

\* cited by examiner

EX VIVO METHODS FOR DRUG DISCOVERY, DEVELOPMENT AND TESTING

RELATED APPLICATIONS

This application claims priority, under 35 U.S.C. § 119(e), to U.S. Provisional Patent Application No. 60/736,495, filed Nov. 14, 2005, incorporated by reference herein in its entirety, and U.S. Provisional Patent Application No. 60/762,180, filed Jan. 24, 2006, incorporated by reference herein in its entirety.

FIELD

The disclosure relates to methods for assessing absorption, transport, metabolism, elimination, efficacy and/or toxicity of substances, such as chemical compounds and, particularly, drugs and drug candidates, by perfusing organs and tissues ex vivo with compatible solutions containing the substances. The methods include assessing anything, including, but not limited to, absorption, transport, metabolism, elimination, efficacy and/or toxicity with regard to particular tissues or organs, including liver, kidney, intestine, lung, heart and pancreas, or to controlled combinations of organs, whereby the perfusate effluent from one organ forms the perfusate influx for a different organ or whereby organs are perfused by a common perfusate in parallel. Methods of the invention permit absorption, transport, metabolism, elimination, efficacy and/or toxicity assessment of substances using human tissues or organs, particularly organs unsuitable for transplantation, on an organ-by-organ basis, in contrast with and, optionally, supplemental to, in vivo, i.e., non-human animal, testing.

BACKGROUND

Methodologies available for assessing the absorption, transport, metabolism, elimination, efficacy and toxicity of substances, such as drugs and drug candidates, span many levels of mammalian organization from in vivo studies to isolated organs or tissues, tissue slices, cultured cell types, subcellular particles, multi-enzyme complexes and molecular interactions. In practice, these complex methods result in considerable wasted time, effort and resources in many fields, particularly drug development, where drug candidates may undergo several rounds of safety and efficacy testing only to find that later testing or market experience reveals undesirable effects often with tragic consequences. For example, drugs that have been approved for human use, but later recalled due to toxicity issues include Vioxx®, Celebrex®, phexophenadine and thalidomide.

In early clinical trials, adverse benefit/risk ratios frequently cause the demise of otherwise promising pharmacologically active substances. Such events are costly and can have a profound effect on drug discovery, health care and industry stability and economics. Historically, attempts to weed-out substances having an unacceptable benefit/risk ratio have relied on in vivo non-human animal studies using several species, such as rodent species.

Limitations of toxicity studies in non-human species have long been, and still are, well recognized in the pharmaceutical industry, but short of performing toxicity studies in humans in vivo there has been no viable alternative. Attempts have been made to bridge the gap between non-human testing and humans using tissue preparations including subcellular particles, e.g., microsomes, primary cells and cells in culture, e.g., hepatocytes, and tissue slices. Although these in vitro tissue preparations generate much useful data, they have not made a significant difference in the number of drug candidates failing in clinical trials due to adverse risk issues. There is ample evidence in the literature to suggest that this is due, at least in part, to the fact that the farther the tissue preparation is from the whole organism, the greater the risk of false positives and false negatives. For example, false positives or false negatives may occur when assessing whether such test substances administered in therapeutic doses are toxic when administered alone or with other co-administered drugs. Moreover, there is no guarantee that pharmacokinetic/toxicity relationships in normal human tissues determined in vitro will be the same as in diseased human tissues in vivo.

As it is not ethical to use humans for exploratory toxicity testing, the choice has been to perform in vivo testing on a variety of non-human animal species and/or in vitro testing using human biological samples. It is recognized that the confidence in the safety and efficacy of a drug compound increases as it moves from preclinical to clinical testing. It is also recognized, however, that the dangers of unforeseen deleterious results also increase.

Thus, there is a need for improved methods for evaluating absorption, transport, metabolism, elimination, efficacy and/or toxicity of substances, such as drug candidates, that bridge the gap between in vivo non-human animal testing and human administration. In addition, there is a need, in the drug development industry, for new and improved methods of evaluating potential drug candidates early in the research and development process, and providing such evaluations to drug development companies.

SUMMARY

Embodiments of the invention fulfill needs in drug development and testing industry for absorption, transport, metabolism, elimination, efficacy and/or toxicity and other testing of substances, such as drug candidates developed for human administration, by providing perfused tissues or organs, preferably, perfused human tissues or organs, more preferably, perfused human organs and organ sets for ex vivo testing.

Methods provided herein bridge the gap between in vitro testing on human biological samples and in vivo testing in non-human animals. As noted above, current testing methods, while beneficial, are not fully competent for identifying compounds that are toxic or have other deleterious effects in humans. Because in vivo human studies are ethically limited and frequently lead to unsatisfactory results, methods provided herein reduce the chance of unforeseen morbidity and mortality related to clinical testing of substances, such as lead drug candidates. Consequently, data showing the fates and effects of drugs in perfused human organs and tissues are more reliable and clinically relevant than data from in vitro systems that lack a blood supply and full complement of integrated cell types or in vivo non-human animal models.

To this end, embodiments of the invention include methods for performing absorption, transport, metabolism, elimination, efficacy and/or toxicity testing of substances, such as chemical compounds and, most particularly, drugs and drug candidates, ex vivo on human tissues or organs. Such testing provides an assessment of safety and/or other characteristics of the substances or metabolites thereof.

Embodiments include methods for perfusing tissues or organs, preferably, human tissues or organs, more preferably, human organs, and most preferably, human organs unsuitable for transplantation including diseased or defective organs or organs having a lower than acceptable likelihood of successful transplantation due to, inter alia, prolonged warm ischemia times, with a perfusate comprising at least one substance for assessment, as well as methods for identifying metabolites of the substance.

Embodiments provide methods of determining the fates and effects of substances, such as a chemical compound, in ex vivo perfused intestine, lung, liver, kidney or heart with respect to: rate and extent of substance absorption; extraction; identification of metabolites; organ control of the concentration of the substance and/or metabolites in plasma; tissue binding and accumulation; and tissue clearance and elimination.

In embodiments, the invention provides methods of determining absorption, transport, metabolism, elimination, efficacy or toxicity of a test substance on at least one tissue or organ, comprising:

a) perfusing at least one tissue or organ with a medical fluid to preserve said tissue or organ in the presence and absence of at least one test substance; and b) comparing the tissue or organ in the presence and absence of the test substance to detect the absorption, transport, metabolism, elimination, efficacy and/or toxicity of the test substance in the tissue or organ. Preferably, the tissue or organ is a human tissue or organ, more preferably, a human organ, such as liver, lung, kidney, intestine, heart, pancreas, testes, placenta, thymus, adrenal gland, arteries, veins, lymph nodes, bone or skeletal muscle.

In embodiments, the tissue or organ is perfused with a first medical fluid that does not comprise a test substance, followed by perfusion with a second medical fluid comprising a test substance. The medical fluids can be the same (but for the presence of the test substance) or different or adapted to identify the effects of the test substance on absorption, transport, metabolism, elimination, efficacy and/or toxicity in the tissue or organ. In embodiments, absorption, transport, metabolism, elimination, efficacy and/or toxicity may be detected morphologically or histochemically, preferably, immunohistochemically, by analyzing biopsy samples and detecting changes or lesions therein.

In embodiments, absorption, transport, metabolism, elimination, efficacy and/or toxicity is detected biochemically by assaying for toxic metabolites or end-products or for the liberation into the perfusate of intracellular molecules, such as enzymes, for example, lactate dehydrogenase, that are indicative of effects of the test substance, particularly toxicity.

In embodiments, absorption, transport, metabolism, elimination, efficacy and/or toxicity is detected by changes in gene expression in cells comprising the perfused tissue or organ by, for example, in situ hybridization with a probe that specifically hybridizes to at least one mRNA-encoded gene expressed by the tissue or organ. Assays for cell death, particularly apoptosis and necrosis, indicative of future toxic effect, may be performed.

Preferably, the tissue or organ is perfused under physiological temperature, pressure, oxygenation, osmolality, electrolyte balance and pH. In embodiments, the perfusate comprises matched human erythrocytes in a physiologically-acceptable medical fluid. The medical fluid advantageously further comprises about 2 to about 6% human serum albumin, N-acetylcysteine, adenosine monophosphate (AMP) and/or superoxide dismutase. In certain organs, such as the heart and liver, nervous stimulation may be provided as well during perfusion. In embodiments, wherein the organ is a liver, the medical fluid may comprise secretin or bile acids. In embodiments, wherein the organ is a kidney, the medical fluid may comprise a mixture of essential and non-essential amino acids. In embodiments wherein the organ is intestine, the medical fluid may comprise dexamethasone or noradrenaline.

Absorption, transport, metabolism, elimination, efficacy and/or toxicity of the test substance may be detected by assaying an effluent from the perfused organ. Preferably, the perfusion effluent is a functional effluent depending on the organ, such as kidney urine, liver bile or lung mucus or an effluent comprising pancreatic exocrine digestive enzymes. In embodiments, the effluent may be assayed after it is recovered leaving the organ via a vein, such as insulin and glucagons from the pancreas, albumin and glucose from the liver, oxygen and carbon dioxide from the lung or creatinine from the kidney. In the heart and intestine, effects of a test substance, particularly toxic effects, may be detected by a motor response, such as heartbeat and peristalsis. Additionally, absorption, transport, metabolism, elimination, efficacy and/or toxicity may be detected in any organ by changes in vascular resistance, and, specifically with regard to toxicity testing in the lungs, by changes in respiratory compliance.

Embodiments also provide methods for assembling experimental data obtained from the perfusion studies in a database and using that information to model the effectiveness of substances, such as drugs and drug candidates, in silico by matching structural features of the substances with biological effects. Thus, methods can correlate the absorption, transport, metabolism, elimination, efficacy and/or toxicity of the test substance with structural, physical or other chemical features of a plurality of test compounds in a database, thereby providing methods of intelligent drug design and in vitro and in vivo protocol design for drug discovery and clinical trials. Methods of the invention provide improved access to information and drug/effect correlations, because the information is obtained from ex vivo tests using perfused organs and tissues rather than from in vitro testing or in vivo non-human animal studies.

Methods provided by the invention advantageously avoid the inherent species differences in test substance absorption, transport, metabolism, elimination, efficacy, toxicity and tissue susceptibility encountered when using non-human animal models to mimic in vivo activity and behavior in humans. In addition, perfused human tissues or organs can be exposed to drugs or drug candidates and metabolites thereof under physiological conditions and at clinically relevant concentrations to all cell types in the tissue or organ, thereby providing more reliable, accurate and consistent results.

Methods of the invention are advantageous compared to in vitro systems because they include all cell types in their normal proportions and orientations with respect to blood and tissue. Thus, substances, such as drugs and drug candidates, can be delivered as they would be in vivo, wherein the cell types retain their phenotype in the whole organ. Inventive methods are advantageous compared to in vivo studies, even when possible to be performed in humans, because the contribution of individual tissues or organs to the fates and effects of test substances, such as drugs and drug candidates, can be assessed, thereby providing information useful in drug discovery and development.

Embodiments of the present invention include methods for evaluating a substance comprising passing a substance to be evaluated through a metabolically active human organ that has been permanently removed from its origin, collecting data from the organ and using the collected data to evaluate the substance.

In embodiments, the substance is a pharmaceutical, the evaluation is part of a governmental and/or regulatory approval process; the organ, which may be diseased is selected from the group consisting of: liver, kidney, lung, intestine, pancreas and heart; and data are collected by evaluating a perfusate that comprises the substance and has exited the organ or by evaluating a biopsy taken from the organ.

In embodiments, the evaluation method comprises passing a second substance through the organ after the first substance and collecting data on the interaction of the first and second substances.

In embodiments, the evaluation method comprises perfusing the organ with a first fluid that does not contain the substance and then with a second fluid that contains the substance.

Embodiments of the invention include methods of collecting data as part of a governmental regulatory approval process comprising: providing an isolated metabolically active human organ from a living or deceased human; perfusing through the organ a perfusate containing a test substance to be evaluated; collecting data from the perfusate and organ; and using data collected as part of a submission to a governmental regulatory organization.

In embodiments, the method of collecting data comprises using the data as part of a process to resolve conflicting data across species, assess a compound's toxicity, determine the presence of metabolites, and/or assess a compound's bioavailability, absorption, therapeutic effects and/or drug-drug interactions. The organ is preferably selected from the group consisting of: liver, kidney, lung, intestine, pancreas and heart.

Embodiments of the invention include methods of developing pharmaceutical products comprising passing a drug candidate through a metabolically active human organ that has been permanently removed from its origin; collecting data from the organ; and using collected data as part of an evaluation to determine whether to continue developing the drug candidate into a pharmaceutical. The data can be used to evaluate at least one parameter of the drug candidate selected from the group consisting of: absorption, toxicity, drug-drug interactions, therapeutic effects, presence of metabolites and liver clearance. The data can also be used in at least one drug development phase selected from the group consisting of: discovery, pre-clinical, phase I, phase II, phase III and phase IV.

Embodiments of the invention include methods of generating revenue comprising charging a fee to a third party for performing an evaluation process on a drug candidate; passing the drug candidate through a metabolically active human organ that has been removed from its origin; collecting data from the organ; and providing the data to the third party.

In methods of generating revenue, data can be provided in raw form or evaluated before it is provided to the third party. The data can be used as part of a governmental and/or regulatory submission. The data can be owned by the party performing the evaluation or the party requesting the evaluation. The data can be used by the third party during at least one drug development phase selected from the group consisting of: discovery, pre-clinical, phase I, phase II, phase III and phase IV. The fee may be a lump sum payment or a percentage of sales of the resulting pharmaceutical.

Embodiments of the invention include methods of reducing the cost to develop pharmaceuticals comprising screening compounds by passing the compounds through at least part of a metabolically active human organ that has been permanently removed from its origin and determining whether to pursue pharmaceutical development of the compound. Thus, methods of reducing the cost can include not developing a pharmaceutical based, at least in part, on data generated by passing the compound through the organ and/or ranking potential pharmaceuticals based on data generated by the screening process.

Embodiments provide methods of developing generic pharmaceuticals comprising generating data for inclusion in a submission of a generic pharmaceutical approval process by passing a pharmaceutical through a metabolically active human organ that has been removed from its origin.

Embodiments provide information products. Such information products may comprise data relating to a pharmaceutical product that is generated, at least in part, by passing the pharmaceutical product through a metabolically active human organ that has been removed from its origin. In embodiments, the information product is provided in a computer-readable form.

Embodiments provide methods of marketing an information product comprising providing to a third party an evaluation of at least one economic effect of the information product on the development of a pharmaceutical by the third party.

In embodiments of methods of marketing, evaluation of the economic effect of the information product may be based on assumptions, wherein the evaluation may include an economic effect of the information product on a problem encountered during development of a test substance. The economic effect may include a total value of the information product, which may be adjusted for the probability that the total value will be achieved. The total value of the information product may include additional profits from sales of the substance as a pharmaceutical, for example, where the pharmaceutical would not have been launched without the information product. The total value of the information product may also include an amount of additional peak sales of the substance from a decrease in time to develop the substance due to the information product. The decreased time to develop the substance may include, at least in part, time to resolve a problem encountered during development. In addition, the total value of the information product may include decreased costs to develop the substance due to the information product. Decreased costs may be due, at least in part, to testing obviated by the information product.

Embodiments provide methods of evaluating a substance, comprising: providing a substance to be evaluated and analyzing compound data collected from passing the substance through a metabolically active human organ that has been permanently removed from its origin.

In embodiments of methods of evaluating a substance, the substance is a pharmaceutical. The data may be used as part of a submission to a governmental and/or regulatory organization, as part of a process to resolve conflicting data across species or to assess the presence of metabolites or the compound's bioavailability, absorption, therapeutic effects, drug-drug interactions and/or liver clearance. In addition, the data may be used to select appropriate patients for testing the substance in clinical trials and/or to select the formulation of the substance that should be used in clinical trials.

Additional features and advantages of the present invention are described in, and will be apparent from, the following detailed description.

DETAILED DESCRIPTION

Embodiments of the invention include methods for using tissues or organs, preferably, human tissues or organs, more preferably, human organs, to determine the absorption, transport, metabolism, elimination, efficacy and/or toxicity of a compound or substance, preferably a chemical compound, more preferably, a pharmaceutical drug or drug candidate. Preferred tissues and organs include, but are not limited to, liver, lung, kidney, intestine, heart, testes, placenta, thymus, adrenal gland, arteries, veins, lymph nodes, bone and skeletal muscle.

As used herein, the terms "absorption," "transport," "metabolism" and "elimination" are understood to apply to any tissue or organ employed, but are specifically relevant to certain tissues and organs used in perfusion-based testing. For example, absorption is particularly relevant to the intestines and lungs; whereas transport, such as plasma clearance and metabolism, although also relevant to the intestines and lungs, is particularly relevant to the liver, kidneys and heart. Elimination is particularly relevant to the intestines, liver, kidneys and lungs.

As used herein, the term "toxicity" encompasses physical, chemical, biochemical and biological damage to tissue or organs, including at the cellular level. Toxicity is related to deleterious effects on tissues and organs, including, but not limited to cell death, apoptosis, genetic mutation, changes in gene expression, biochemical inhibition, reductions in metabolism, induction and oxidative damage, as well as deleterious effects resulting from drug-drug interactions. As provided herein, methods of the invention include detecting tissue- or organ-specific biomarkers for acute or chronic toxicity induced by a test compound, such as a drug or drug candidate.

The term "efficacy" encompasses a measure of the positive, homeostatic or health-promoting effects of a test compound, such as a drug or drug candidate, on a tissue or organ, preferably, human tissue or organ. Such measures include, but are not limited to, assays for reducing or eliminating disease-specific biomarkers, preferably using diseased organs or organs infected by a pathogen. In certain embodiments, the biomarker is a pathogen-associated marker of either pathogen or cellular origin, the reduction or elimination of which indicates that the test compound may be effective as an anti-pathogenic agent. Conversely, in embodiments, the biomarker may be a breakdown product or other indicator of an anti-pathogenic effect, wherein an increase in the biomarker evidences the efficacy of the test compound as an anti-pathogenic agent. Thus, evaluating different tissues or organs with a test compound may provide evidence of the compound's efficacy and/or beneficial effects.

As provided herein, methods of determining absorption, transport, metabolism, elimination, efficacy or toxicity of a test compound comprise: contacting a tissue or organ, preferably, human tissue or organ, with a test substance by perfusion of the tissue or organ with a medical fluid containing the test substance. The terms "test substance," "test compound," "substance" and "compound" are used interchangeably and encompass drugs (also referred to as pharmaceuticals) and drug candidates (also referred to as lead candidates or lead compounds).

Perfusion preservation is applied routinely to organs for clinical transplant, wherein perfusion at hypothermic arrest (about 4° C. to about 8° C.) is the preferred method of preservation. In contrast, organ preservation for transplant under physiologic conditions, including normal body temperature (normothermia), although studied at length, has not been clinically applied because it is difficult in practical applications to maintain an organ at normal body temperature. To some extent, the application of normothermia has been limited by the high demands placed on a transplanted organ, specifically that it be both maximally functional and minimally inflammatory. Because demands of transplantation are reduced or non-existent in ex vivo absorption, transport, metabolism, elimination, efficacy and/or toxicity testing, many of the limitations of normothermia are overcome. Specifically, ex vivo normothermic organs may be supplied with oxygen via type-matched blood cells without concerns of immunogenicity, and may acceptably experience degraded functionality during normothermic perfusion, e.g., as toxins normally cleared by other organs accumulate and as substrates and factors normally produced by other organs are depleted.

Embodiments include business methods and models of using features of the present invention to improve drug development, reduce costs and/or generate revenue. For example, the methods can include making available to a third party a service including conducting testing as part of a drug development program. Embodiments include making available to a third party the resulting data and/or information generated from that testing in the form of an information product. The service and product may be made available to a third party for a fee. It should be appreciated that a fee may include a fixed amount or lump sum, an amount that is based on a variable, such as a percentage of the profits of the sale of a product, or any other suitable form of remuneration, compensation or reimbursement. Accordingly, an entity that conducts testing according to the disclosed methods and generates data and information from the disclosed methods, referred to herein as a provider, may generate revenue from marketing and selling services and products described herein to third parties.

As described above, embodiments of methods include a preservation stage in which one or more organs or tissues from a target species, such as a human, are preserved under hypothermic conditions such that the organs or tissues maintain the capacity to resume and sustain substantially normal metabolic activity and function upon return to physiologic temperature. As used herein, the term "metabolically active" refers to demonstrating a level of biochemical activity characteristic of a living organism.

In a functional stage, organs or tissues may be perfused with a normothermic blood or blood-based perfusate to stabilize the organ or tissue physiology. The physiology and biochemistry of the organ or tissue is preferably maintained substantially in accordance with the physiology and biochemistry of an organ or tissue in vivo, such that data generated from the testing is substantially unequivocal, reproducible and relevant. In whole organs, for example, cells retain their phenotypes, cell types are present in their normal proportions and orientations with respect to blood and tissue, and compounds are delivered as they would be delivered in vivo.

The functional state of test organs or tissues may be quantified by the inclusion of positive and negative controls. The controls may be added either simultaneously with the test compounds or after substantially all the essential samples required for analysis of the fate and effects of test compounds have been collected. A fluid or perfusate that does not contain the substance may be passed through the organ before and/or after perfusing the organ or tissue with a second fluid that contains the substance. In this way, the organ may act as its own control. The choice of positive and/or negative controls used depends on the primary objective of each study.

Embodiments of methods may be conducted in "normal" and "diseased" organs and tissues wherein the physiology and biochemistry of each organ or tissue is maintained as close as possible to in vivo characteristics and properties for that particular disease or condition. Embodiments of methods may comprise use of multiple proprietary medical devices, solutions and protocols, including the sourcing, procuring, preservation and evaluation of research organs and/or tissues.

Exposing a substance to metabolically active extracorporeal tissues or organs, other substances or combinations thereof, according to methods disclosed herein, generates data and information. Such data and information may be stored on any computer-readable medium and/or in any other suitable form. Such data and information may be considered a transferable information product.

In one aspect, the disclosed methods may generate data and information about a substance. As used herein, a substance can include any product or component thereof. In particular, the substance can include a compound of interest in the development of a product such as a pharmaceutical product. Data or information about the substance may include characteristics of the substance itself, its derivatives, metabolites and/or other related substances.

Data or information obtained about the substance may include the effects of the substance on ex vivo organs or tissues, the effects of ex vivo organs or tissues on the substance and the effects of the substance on other substances exposed to the ex vivo organs or tissues. Information about the substance and its effects may include, but is not limited to, tissue or organ absorption, transport, metabolism, elimination, pharmacokinetics and bioavailability, toxicity, efficacy, metabolites, metabolite pharmacokinetics, metabolite toxicity, metabolite efficacy, interactions with other substances, and other reactions and products of those reactions for assessing usefulness or other characteristics of the substances or the metabolites or derivatives thereof.

In another aspect, disclosed methods may generate data and information about the ex vivo organ or tissue exposed to the substance. In applications of disclosed methods, testing results may provide data and information on classes of compounds, receptors, biochemical pathways, physiological and pathological mechanisms, biomarkers and other phenomena associated with living organisms. Accumulated data and information generated in performing disclosed methods may create a resource of statistically significant and scientifically valid information. Each of these forms of data and information constitutes a transferable information product.

In embodiments, an information product provided to a third party may include raw data generated from performing disclosed methods. Alternatively, or in addition, an information product provided to a third party may include an interpretation or evaluation of raw data in various levels of useful and/or conclusory forms. Raw data may be retained as proprietary by the provider, and only information derived from the raw data may be made available as an information product to the third party. Therefore, in addition to the service of conducting the testing according to disclosed methods and generating raw data, a provider may interpret data for a third party.

Data or information about a substance derived from performing at least one of the disclosed methods may be used in numerous ways, thereby conveying value to the information product. Data or information may, for example, be used to determine whether the substance has a potential beneficial use, whether the substance has potential to be used for a particular purpose, or to what degree the substance has potential to be used for a particular purpose. For example, data collected from exposing a substance to a metabolically active extracorporeal tissue or organ according to disclosed methods may be used to determine if the substance should undergo further testing to determine its usefulness as a pharmaceutical product. To this end, data and information may be used to eliminate non-useful substances from a population or pool or group of substances. It should be appreciated that determining that a substance is not useful for a particular candidate application is of significant value allowing allocation of resources to further the development of those substances that are identified as being potentially useful, for example.

An information product may be used by a third party such as a drug developer involved in the development of products such as pharmaceuticals. The drug developer may supply one or more substances to the provider for testing. The substances supplied to the provider may be substances identified at any stage of the drug development process including after the drug has been developed. The drug development process typically includes a series of steps, stages or phases associated with different levels of testing. The phases can include the discovery phase, pre-clinical phase, the clinical phases and the post-approval and post-marketing phases. At each phase in the development process, a drug developer incurs significant cost for each substance carried forward to the next phase. Included in the cost to the drug developer are direct expenses associated with conducting testing. For example, by the time a substance has advanced through the pre-clinical phase of testing, a substantial amount of money has been spent on that substance. By phase IIb, a drug developer has already spent usually more than three years in clinical trials and typically nearly $40 million testing the compound in humans.

In addition, there are indirect costs associated with delays in advancing beneficial compounds to market. Problems such as conflicting data, uncertainty about results, and unexpected problems all require additional testing during which sales, including peak sales, of the drug could have occurred. There are also indirect costs associated with decreased yield from profits on the sale of compounds not developed. In other words, for every efficacious and safe drug that is not developed, for every day a drug remains off the market, for every additional test that must be performed on a compound, there is a cost to the drug developer.

Information products of disclosed methods may provide definitive, relevant, organ-specific, species-specific data to address problems which can occur during each of the phases of research and development. Information products of disclosed methods may guide drug candidate selection, facilitate problem-solving such as discrepancies in data or information obtained from other types of testing, and may expedite regulatory approval throughout development and compliance processes and for regulatory compliance.

Information products may create value and efficiency in the drug research and development process in at least four ways. First, information products may increase the number of substances that can be used and sold as pharmaceutical products by potentially providing more and better data earlier in the research and development process. Second, information products may increase the days of peak sales by potentially shortening the time necessary to advance products to market. Third, information products may reduce development costs by avoiding returns to earlier phases due to unexpected problems later in the process, as well as potentially reducing the overall time to market. Fourth, information products may contribute to protecting humans from toxic side effects during clinical testing of substances in the development process and during use of the released substance.

In the discovery phase, substances are synthesized and purified for screening and testing at the sub-cellular and cellular levels to identify those substances with potential beneficial uses. Screening methods during the discovery phase can include high-throughput testing using combinatorial chemistry to create and test numerous different molecules. Other screening methods can include chemical genomics and bioinformatics. Chemical genomics rapidly characterizes a large pool of small molecules against target cells or tissues. Bioinformatics, or in silico biology, is used to gather gene and protein sequence data from different life forms to compare potential treatments, known gene function and biologically active binding sites through computer analysis to identify similarities or patterns. Information products of the invention may dramatically increase the pool of potentially useful compounds at the discovery phase of the research and development pipeline. In the discovery phase, information products may resolve problems such as conflicting data from high-throughput testing which may be poorly predictive of efficacy. In addition, by offering the prospect of less extrapolation and more comprehensive screening of target compounds than existing in silico models, information products and in silico models generated therefrom may allow a drug developer to much more accurately target compounds in the early stages of discovery.

Potentially useful compounds synthesized, purified and preliminarily screened for potential usefulness in the discovery phase may enter the pre-clinical phase. The pre-clinical phase typically includes testing of substances in in vitro models using cells and tissue slices and in animals to determine information about the substances and their effects.

Information products of the disclosed methods enable the drug developer to identify the most-promising compounds and to reconcile or resolve discrepancies in data or information obtained from other types of testing. Animal models employed in the pre-clinical phase of drug development can be imperfect models for how a substance actually acts and is acted upon in a human. For popular therapeutic areas such as oncology and neurology, animal models are particularly misrepresentative of humans, as evidenced by the high attrition of substances directed to those therapies through the clinical phases. As a result of animal and in vitro testing often being poorly representative of humans, the research and development process frequently does not identify the best lead compounds from a family of compounds in the early stages of development.

Information products of disclosed methods may provide value to the drug developer by minimizing delays in the development of a drug and shortening the period of time required to release a drug, thereby increasing the days of peak sales of the developed drug. To this end, earlier identification by disclosed methods reduces the risk of being beaten to market by a competitor and provides the drug more time under patent protection, resulting in additional peak sales. If a drug which will ultimately have annual peak sales of $580 million, for example, must be returned to pre-clinical testing due to unexpected problems such as unexpected metabolites unable to be predicted in pre-clinical animal studies but that emerge in human clinical trials, the cost to the drug developer for every month of delay is significant. Information products, therefore, minimize or eliminate delays associated with uncertainties caused by unsuccessful animal-to-human extrapolation and maximize the value of peak sales of the drug.

Additionally, animal studies often yield conflicting data across species. Indeed, in the pre-clinical phase of drug development, common problems include false negatives and false positives, conflicting absorption, toxicity, or efficacy data across animal species and uncertainty about rank order within families of compounds.

Information products of disclosed methods may provide data or information about a substance and its effects that is not available from other types of testing and, in some cases obviates the need for other types of testing. Information products may improve the correlation between data obtained in the pre-clinical stage and data obtained in the clinical stage of drug development. Therefore, in the pre-clinical phase, information products may minimize and/or resolve conflicting absorption and uptake data across species, conflicting toxicity data across species, uncertainty about absorption and uptake rank order, uncertainty about efficacy rank order, uncertainty about PK-toxicity relationship rank order, uncertainty about drug-drug interaction with specific drugs and rank order and conflicting efficacy data across species. It should be appreciated that distinguishing less-promising compounds from more promising compounds at this stage or earlier in the process saves the delay and cost to the drug developer of further testing compounds with minimal potential. This allows the drug developer to allocate more resources toward the more promising compounds to advance them efficiently through the later stages of the development process and minimize, if not avoid, bringing toxic compounds into clinical trials. Information products may also be used to select appropriate patients for clinical trials based on parameters of the test substance, sensitivity to the substance or any other suitable factor. In addition, information products may be used to select which of a group of different formulations including the same or different compounds should be used in clinical trials.

Potentially useful substances found to have desirable safety and efficacy characteristics in various animal models may enter the human clinical phase of drug development. The clinical phase includes at least four phases: phase I, phase IIa, phase IIb and phase III. Phase I testing involves the initial introduction of the potentially useful substance into a human clinical test subject. Phase I testing is used to determine characteristics of the substance in humans, such as its metabolism, structure-activity relationships, mechanism of action and other pharmacokinetic and pharmacological data. In addition, phase I testing provides metabolic and pharmacologic actions and side effects of the substance in humans. Phase I studies may further determine if the substance can be used as a research tool to study biological phenomena or disease processes or to further define the testing to be performed during phase II. In phase I clinical testing, common problems include the emergence of unexpected metabolites and unexpected problems with bioavailability due to low absorption and/or high metabolism. Such problems indicate that animal studies conducted in pre-clinical testing were not sufficiently representative of human conditions to adequately predict problems encountered in humans. Therefore, information products of disclosed methods provide a drug developer a tool to further test the compounds in an environment more representative of the human condition without further risk to the life or well-being of clinical test subjects. Furthermore, the contribution of an individual organ to the fate and effects of substances can be quantified in information products.

Application of information products to problems encountered in the pre-clinical phase and phase I for substances in high-potential therapeutic areas is especially effective and has the potential to fundamentally improve the pharmaceutical research and development process. Accordingly, information products of disclosed methods provide great values in early stages of drug development such as in pre-clinical and phase I clinical stages of development. Information products of disclosed methods may be particularly designed to resolve problems arising in the pre-clinical phase and phase I including conflicting absorption, toxicity, and/or efficacy data across animal species, uncertainty about rank order within a family of compounds related to absorption, efficacy, and PK-toxicity relationship, and uncertainty about drug-drug interactions in the pre-clinical phase and unexpected problems with bioavailability and uncertainty about surprise metabolites in phase I or later.

Phase II testing is performed in a larger population of clinical test subjects than phase I in order to generate preliminary data on the effectiveness of the drug for a particular indication or indications in individuals with such a disease or condition. In addition, phase II testing can provide information on short-term toxicity and side effects of the substance. Common problems in phase II of clinical testing include uncertainty about magnitude of therapeutic effect for estimation of the number of test subjects, and uncertainty about correct inclusion/exclusion criteria based on drug-drug interaction. If a substance demonstrates favorable characteristics based on phase II studies, e.g., effectiveness with minimal or tolerable side effects, the substance may proceed to phase III human clinical testing. Phase III clinical testing enables the drug developer to expand the data of the efficacy and toxicity of the drug to fully assess the risk-benefit relationship of the use of the drug in humans. Phase III also provides a basis for extrapolating the data and findings in relatively small populations of test subjects exposed to the substance to a broad population of subjects who may benefit from use of the substance. At each of these late-stage clinical phases, an information product may, for example, be further used by a drug developer to resolve any issues associated with efficacy, unexpected side effects, toxicity, and uncertainty about drug-drug interactions. Even after a drug has been made available to the public, typically referred to as phase IV, long-term follow-up testing may be required to confirm continued usefulness of the drug, long-term toxicity or in product line extension development which can be addressed using the information product. This further testing may be performed in accordance with regulatory compliance.

Late-stage failures of substances occur, in large part, because of the limited ability of existing methods, such as animal testing in the pre-clinical phase, to conclusively predict efficacy and toxicity in humans. In fact, significant attrition of substances occurs in late clinical stages of drug development, primarily in phases IIb and III, indicating that substances are failing to be identified earlier for lacking efficacy (phase III) and for having intolerable levels of toxicity (phase II) in humans. By phase IIb, a typical drug developer has, on average, already spent more than three years in clinical trials and nearly $40 million on testing the substances in humans, a significant loss to any size drug developer. Pursuit of these substances by drug developers often occurs at the expense of pursuing other substances.

Furthermore, investors and analysts tend to follow substances in the later stages of the development process. More specifically, analysts evaluate pharmaceutical research and development almost exclusively on the number of substances under regulatory review, up for filing with a regulatory body, and in, or entering, phase III. To this end, information products of disclosed methods may be used by both small and large pharmaceutical companies to reduce risks associated with missed opportunities of developing a promising drug by choosing the wrong substance and to identify the right substance sooner allowing the drug developer to capture additional peak sales. Enabling the development of substances that would otherwise have not been brought forward is particularly valuable to small pharmaceutical companies which may not have the resources to cycle back and test multiple back-up substances. In addition, both large and small companies alike can benefit from additional peak sale profits from time savings made possible by information products of disclosed methods. Accordingly, by increasing the probability of identifying high numbers of useful substances, and by limiting the number of late-stage failures and unexpected late-stage delays, particularly in phase III, information products provide drug developers important intangible benefits, such as strengthened public trust, investor credibility, and stock market performance, in addition to predicted research and development productivity gains.

In addition to reducing costs preventing further investment in unqualified drugs and resolving conflicting or uncertain data directly impacting the cost of developing a drug, information products of disclosed methods may also contribute to identifying useful products and components thereof. The expected value of substances that would otherwise be abandoned and that are enabled by information products of disclosed methods to move forward in the development process can be significant. The expected value attributed to the application of information products that leads to an approved substance may be based on profits from the substance, additional peak sales from reduced approval time, and cost savings from reducing the number and duplication of tests that are accrued through the development process.

In addition to applying information products of disclosed methods to specific problems in particular phases of drug development, information products may be applied to particular therapeutic areas of drug development. Information products of disclosed methods may impact those therapeutic areas where existing tools, such as animal and in vitro models, are particularly non-predictive and/or where the sales of drugs that are launched are expected to be high. The expected impact of information products of disclosed methods on a particular therapeutic area can be based on, for example, the failure rate from phase I to drug launch, projected sales growth indicating future potential of the therapeutic area, and average sales per high-potential drug indicating the extent of high-potential drugs within a therapeutic area. The failure rate during the clinical phase of drug development reflects the tendency within a therapeutic area to choose the wrong compounds from a family of compounds during the pre-clinical phase of drug development due to animal and in vitro testing being poorly representative of humans.

Information products of disclosed methods may have particular potential relevance and value for "proof of concept" studies, which tend to be organ-specific, and efficacy studies in therapeutic areas for which treatment and testing is organ-specific. In addition to therapeutic areas such as musculoskeletal, inflammatory, gastrointestinal, central nervous system, and vaccines, organ-specific therapeutic areas may include, for example, respiratory, infectious diseases, diabetes/metabolic, oncology, and cardiovascular. For example, disclosed methods may be applied to drug development in the area of oncology where in vitro cancer models are often unable to mimic adequately the architectural and cellular complexity of real tumors. In fact, nine out of every ten attempts to bring a cancer drug to market typically fail. Also, while the extent of high-potential drugs in oncology is smaller than that of its peer therapeutic areas above, oncology is becoming increasingly attractive from a drug sales perspective. Therefore, information products of disclosed methods applied to a therapeutic area where existing tools are particularly non-predictive, but where the sales of drugs that are launched are expected to be high, confer substantial value.

Information products may be used to fulfill requirements to comply with regulations such as governmental regulations, for example, in an approval process or after a substance has been approved for a particular use. At various stages of the drug development process, governmental or other regulatory bodies may require submission of information obtained about a substance. For example, in the United States, the Food and Drug Administration (FDA) reviews the results of laboratory animal and human clinical testing performed by companies to determine if the product intended to be marketed is safe and effective. At the preclinical stage, for example, the regulatory body may conduct a safety review of a potentially useful substance in the form of an investigational new drug application filed with the FDA. Once sufficient data from phase III clinical studies of a substance has been obtained, the studies can be used to file a new drug application with the FDA in accordance with regulations and requirements for marketing the substance as a drug. Even after a single substance is identified and marketed, post-marketing clinical and non-clinical studies along with post-marketing surveillance may be required. To this end, medical, chemical, pharmacological, toxicological, and/or statistical data and other relevant information may be reviewed to determine if further development of the substance should proceed. Accordingly, information products of disclosed methods may constitute information necessary for compliance with regulations by a third party and may be made available to the third party for a fee.

In addition to enhancing the drug development process and providing value to a third party, a provider may create a resource of information based on accumulated data and information generated by the disclosed information. This data and information may include, but is not limited to, information on classes of compounds, receptors, biochemical pathways, physiological mechanisms, and other scientifically valid conclusions. This information may be used to enhance understanding in areas related to or different from drug development. Information products may be in the form of access to this resource of information made available to a third party for a fee. Such information may be used to compare effects in various types of tissues and organs to formulate patterns and models of predictability of those effects. Information products may be used to compare information about the substance and its effects in different tissues and organs, in different species, and in different conditions of tissues and organs such as normal, abnormal, diseased or damaged tissues and organs.

Information products may further be used to formulate models based on statistically significant and scientifically valid data and information accumulated from repeated testing using disclosed methods. In particular, information products may be used to create an in silico model of the effectiveness of a tested compound.

Currently, using advanced computer methods, the effectiveness of drugs and drug candidates can be modeled in silico ("biosimulation") during the early stages of drug development, e.g., during drug discovery, by matching the physical/chemical properties of a compound with various biological events. However, these current methods are limited because most in silico models are built from in vitro data, where the nature of biochemical assays often does not reflect the complexity of the intact human organs or organism. For example, an in vitro-based model may simulate a compound's interaction with one or two pathways, when in reality, the compound also uses several other pathways that are not accounted for in modeling programs informed only by in vitro acquired data. As a result, these in silico models have the same limitations in terms of predictive power as conventional in vitro testing.

Embodiments of the invention provide methods for producing information products that correlate structural, physical and/or chemical characteristics and properties of substances with their fates and/or effects on absorption, transport, metabolism, and/or elimination of the substance, or toxicity thereof. These data are advantageous and an improvement over more conventional in vitro-based methodologies because they more accurately match the in vivo environment, and, more preferably the human in vivo environment, compared with in vitro or non-human animal data. Thus, methods provided herein can produce more accurate in silico models, reducing limitations currently constraining the effectiveness of existing models. For example, significantly less extrapolation from experimental results to expected effects in vivo would be needed. In addition, methods of the invention can be used to evaluate target hits from in vitro-based in silico models, which could then be screened for physiochemical and pharmacokinetic properties. Embodiments of this aspect of the inventive methods can provide more accurate selection of promising pharmaceutical candidates in the earliest stages of discovery for further screening and development. Moreover, ex vivo methods provided herein using intact human organs provide genomic and proteomic analytical screens to identify biomarkers of human disease, toxicity and other pharmacologic activity, as well as time-dependent changes in enzymes and proteins (proteomics) in perfusate secretions and biopsies from metabolically-active isolated perfused human organs under physiologic conditions.

Accordingly, information products may include data needed to formulate an in silico model and may be made available to a third party for a fee. Alternatively, information products may include in silico models developed by the provider and may be made available to a third party for a fee.

Application of disclosed methods to generate information products may be tailored to individual needs of a company. To this end, an evaluation of the drugs under development by a drug developer, such as a pharmaceutical company, may be conducted. The evaluation may further include an effect information products may have on the drug development process of the third party. In this regard, the evaluation may be a prospective evaluation. In addition, or alternatively, the evaluation may include an effect of information products on the drug development process of a third party. In this regard, the evaluation may be a retrospective evaluation. An evaluation may be performed at any suitable stage of the drug development process or the life of the drug on the market to determine the effect or the potential effect of the information product on drug development and use.

An evaluation may be conducted in order to market information products. In this regard, a provider may make available to a third party an evaluation that includes an economic effect of an information product on the drug development process. Alternatively, an evaluation may be conducted for any other suitable purpose. An evaluation may be conducted for a fee in addition to, or, alternatively, included in, any of the fees discussed herein or combinations thereof.

More specifically, an evaluation may include determining where and in what situations a drug developer is expected to extract the most value from employing an information product of a disclosed method. Assessing the impact of disclosed methods on specific problems in each phase of the research and development process contributes to this determination. Additionally, a comparative analysis of different scenarios and assumptions at large versus small companies may suggest differences in the potential sources of value for each, based on differences in their research and development processes and resources. Such an evaluation may take into consideration the percentage of the company's pre-clinical research programs that are in therapeutic areas where information products of disclosed methods may be expected to generate meaningful efficacy data. In addition, an evaluation may reveal where there is an opportunity to leverage the ability of information products of disclosed methods to resolve conflicting species data as a way to increase or reverse a declining trend in the number of investigational new drug applications. An evaluation may also determine the number and type of studies that may provide the most benefit to the company. This evaluation may be based on the average number of compounds brought forward each year from pre-clinical into phase I. Moreover, the evaluation may reveal unexpected problems with bioavailability and toxicity that information products of disclosed methods may resolve based on the number of phase I compounds that have been in the phase longer than the industry average.

The evaluation may estimate the total value of the successful application of an information product of a disclosed method. The total maximum value of the information product may include values associated with yield, time, and cost. Yield may, for example, be measured by profits from launched or fully developed incremental compounds that would not have been uncovered and brought forward without the information product. Time may be measured in terms of additional peak sales realized from resolving the problem or situation more quickly by using the information product. Cost may be related to decreased expenses associated with reducing the amount of testing such as the number of trials and/or the number of repeated trials. The values of yield, time and cost can, therefore, be summed to determine the total maximum value of the information product. The expected value takes into account probabilities associated with the likelihood that the total maximum value of the information product will be realized.

The evaluation may estimate the total value of the successful application of an information product of a disclosed method against a range of common problems such as problems associated with each stage of drug development. The problems may include conflicting data from high throughput testing in the discovery phase; uncertainty about efficacy rank order, conflicting absorption and uptake data across species, conflicting toxicity data across species, conflicting efficacy data across species, uncertainty about PK-toxicity relationship rank order, uncertainty about drug-drug interaction rank order, and uncertainty about absorption, and uptake rank order in the pre-clinical phase; unexpected problems with bioavailability due to low absorption and/or high metabolism and uncertainty about appearance of surprise metabolites in phase I; unexpected problems with PKIPD (pharmacokinetic divided by pharmacodynamic) due to species differences, differences between healthy volunteers and diseased patients, difficulty getting enough subjects for trials, uncertainty about magnitude of therapeutic effect for estimation of sample size, and uncertainty about correct inclusion/exclusion criteria in phase II; difficulty getting enough subjects for trials, uncertainty about magnitude of therapeutic effect for estimation of sample size, and uncertainty about correct inclusion/exclusion criteria in phase III. In each situation or problem encountered in the development process of a drug the expected value of the information product may result in additional compounds that would not have otherwise been pursued, additional profits due to time savings and firm cost savings associated with a decreased amount of required testing. The expected value of the information product can be expected to derive from at least one of these sources and other sources.

For each situation or problem that arises during the development process, one can determine a total maximum value and an estimated expected value of the effect of the information product on resolving the problem. If, for example, a problem arises in the development of a drug that requires a drug developer to place the compound on hold to resolve the problem, the delay to resolve the problem may result in a loss of peak sales, for example. The total maximum value includes the value the information product confers to the drug developer in resolving the problem. The probability of the problem occurring coupled with the probability that the total maximum value of the information product will be achieved can be used to determine a total value. This relationship between expected value and total maximum value may apply to each situation or problem.

Methods of calculating the expected value of an information product in a particular scenario may include determining a suitable value equation for each situation or problem to which the information product is applied. The value equation may include the total maximum value of the information product.

Determining the expected value of an information product may also include quantifying different base-case assumptions to determine the values of yield time and cost. The evaluation may assume values for parameters such as yields by development phase, duration of each development phase, direct costs by development phase, expected launch year from end of phase, average peak sales per year and years of peak sales. The evaluation may also include values for annual peak sales per launched product, e.g., drug, and/or projected launched products. The evaluation may further include an estimated reasonable discount rate. The assumptions may be determined based on market data from academic articles, web resources, industry interviews or any other reliable source of information.

Methods of evaluation of an information product may include building generic decision trees for each problem or situation encountered in the development process or in a portion of the process. For each situation, a unique decision tree that maps the possible paths of using the information product may be produced. For example, a decision tree for resolving conflicting toxicity data across species as typically encountered in the pre-clinical phase of drug development may be produced. The decision tree may include any number of branches indicating the possible permutations of results that may occur in attempting to resolve the situation. The decision tree may include, for example, a branch for whether additional animal testing will resolve the conflicting toxicity data. If animal testing does not resolve the problem, a decision branch may include whether the information product of a disclosed method resolves the problem. If the information product resolves the problem, a decision branch may include whether the information product includes results that are favorable based on intrinsic properties of the compound, e.g., acceptable toxicity levels. If the information product includes results that are favorable, the decision tree may further include a branch for whether there are any remaining issues that must be resolved that would prevent the compound from moving forward in the development process.

Methods of evaluation of an information product may also include determining and assigning probabilities to each possible result that may occur in each branch of the decision tree. The probabilities at the branches of the decision tree may be based on market data from academic articles, web resources, industry interviews, accumulated data generated from and experience with the disclosed methods and any other reliable source of information. For example, it can be assumed that there is only a 50% probability that additional animal testing will resolve conflicting toxicity data across species and that, if an information product of a disclosed method is applied, the probability of resolving the conflicting data increases to 80%. It can further be assumed that there is a 40% probability that testing using a disclosed method results in a compound having favorable characteristics, i.e., acceptable toxicity levels, and that there is a 20% probability that no other testing needs to be performed to allow the compound to move forward in the development process.

The expected value contributed by an information product may be derived by calculating the total maximum value in terms of yield, time and cost parameters for each situation or tree. The expected value may be calculated based on the probabilities that application of an information product to the problem results in a successful product, e.g., drug, launch. Returning to the example above, if the total maximum value of employing an information product to resolve conflicting toxicity data is $305 million based on the yield, time and cost values, the expected value of the information product may be calculated to be $9.7 million for a single compound, taking into account the probabilities associated with each possible result in resolving the problem ($305 million×50%×80%×40%×20%). Therefore, the information product provides value to a drug developer in resolving problems with particular compounds that are enabled to be developed and released. Information products of disclosed methods offer a potential resource to guard against delays associated with re-testing the compounds. The application of such information products may create an opportunity for loss avoidance against the loss in total maximum value of the product.

EXAMPLES

Perfusion

The nature of the perfusate is preferably adapted to the particular tissue, organ or combination thereof to be tested, or to the chemical or other characteristics of the test compound. For perfusions under hypothermic conditions, the perfusate preferably comprises: calcium chloride, sodium hydroxide, HEPES or other organic acids, phosphate (inorganic or organic ester), mannitol, glucose, sodium gluconate, magnesium gluconate, ribose, starch, glutathione, adenine and water.

A preferred perfusate used in hypothermic conditions, such as KPS-1® (Organ Recovery Systems, Inc., Des Plaines, Ill.), has a pH of about 7.4 and an osmolality of about 330 mOsm and comprises the following components:

| Component | Amount (g/1000 ml) | Concentration (mM) |
| --- | --- | --- |
| Calcium chloride (dehydrate) (ionized) | 0.068 | 0.5 |
| Sodium hydroxide | 0.70 | 18 |
| HEPES (free organic acid) | 2.38 | 10 |
| Potassium phosphate (monobasic) | 3.4 | 25 |
| Mannitol (USP) | 5.4 | 30 |
| Glucose, beta D (+) | 1.80 | 10 |
| Sodium gluconate | 17.45 | 80 |
| Magnesium gluconate D (−) gluconic acid, hemimagnesium salt | 1.13 | 5 |
| Ribose, D (−) | 0.75 | 5 |
| Hydroxyethyl starch (HES) | 50.0 | n/a |
| Glutathione (reduced form) | 0.92 | 3 |
| Adenine (free base) | 0.68 | 5 |
| Sterile water | to 1000 ml volume | n/a |

For perfusions under normothermic conditions, the perfusate preferably comprises: water, sodium, potassium, calcium, magnesium, chloride, buffer component (containing bicarbonate ions and TES, MOPS or BES, for example), glucose, glycerol, choline, amino acid component (such as glutamate, aspartate and/or glutamine), co-enzyme (such as thiamine cocarboxylase), vitaminoid (such as carnitine) and protein (such as insulin). Alternatively, human blood plasma can be used.

A preferred perfusate used in normothermic conditions, such as RS1 (AQIX®, London, England) or OPB-1 or OPB-2 (Organ Recovery Systems, Inc., Des Plaines, Ill.), has a pH ranging from about 7.13 to about 7.41 and an osmolality of about 286 mOsm and comprises the following components:

| OPB-1 Components | OPB-1 Concentrations (mM) |
| --- | --- |
| Organic acids | 5 |
| Chloride | 116.4 |
| Sodium | 135 |
| Calcium (ionized) | 1.2 |
| Potassium | 5 |
| Bicarbonate ions | 25 |
| Glucose | 10 |
| TPP (cocarboxylase) | 0.04 |
| Magnesium (ionized) | 0.45 |
| Glutamine | 0.4 |
| Glutamate | 0.3 |
| Glycerol | 0.11 |
| Carnitine | 0.05 |
| Sterile water | n/a |
| Aspartate | 0.02 |
| Choline | 0.01 |
| Protein (Insulin) | 0.002 (25.00 mIU) |
| Bovine serum albumin | 6% |
| Buffer (BES) | n/a |

Additionally, perfusates can be modified for use with certain organs as described in the following table by way of example.

| Organ | Added Perfusate Component |
| --- | --- |
| Liver | N-acetylcysteine ATP Dibutylcyclic AMP Superoxide dismutase |

| Organ | Added Perfusate Component |
|---|---|
| Intestine | Glycocholic acid |
| | Glycochenodeoxycholic acid |
| | $^3$H-mannitol |
| | Noradrenaline |
| | Dexamethasone |
| Kidney | Methionine |
| | Alanine |
| | Glycine |
| | Serine |
| | Proline |
| | Isoleucine |
| | Mannitol |
| | Creatinine |
| | N-acetylcysteine |
| | ATP |
| | Dibutylcyclic AMP |

Perfusion Study Reports

If a report of the perfusion study results is to be provided to a third party or simply retained, the report can be in draft or final form and contain study information and data including some or all of, but not limited to: description of the experimental procedures including, for example, the perfusion method and preparation details; tissue or organ weight at the start and end of the perfusion study; mass balance data of, for example, radioisotopes in perfusate, plasma, tissue or organ, and/or bodily fluids, such as bile, as applicable; plasma and/or tissue or organ clearance of standards and compounds; excretion of conjugated and unconjugated standards and any applicable conjugates; rate of formation of metabolites of standards and other facets of the metabolic profiles of standards; description of standards, including, for example, metabolic profiles; physiological flow rates at each collection timepoint, e.g., bile, arterial, etc., as applicable; organ donor details and medical records (as permitted); test compound data sheets; test compound receipts and usage records; dosing records; sample collection records; sample weight records; sample storage and shipment records; location of study site; any additional measurements and/or analyses performed during the study or otherwise related to the study; and/or any reports and/or data supplied by a contract facility.

Test Compound Stability Study

Prior to the perfusion study, the stability of the test compound in heparinized blood perfusate should be determined. The test compound is added to recirculating oxygenated human blood perfusate (about 150 ml) at a pH of about 7.4 and a temperature of about 37° C. Aliquots (about 3 ml to about 5 ml) of the perfusate are removed at, for example, 0, 1, 2 and 3 hours post-dosing of the perfusate with a test compound or mixture of compounds. Each aliquot is divided into 2 approximately equal portions—one portion is centrifuged and the plasma removed and frozen at approximately −70° C. and the remaining portion is frozen at approximately −70° C. Samples of perfusate plasma and perfusate can then be analyzed for the test compound and tested to assess the absorption rate of the test compound. The stability study applies to any test compound and any perfused tissue or organ.

Preferred Perfusion Protocols

Set forth below are exemplary assays and organs employing methods of the invention. This disclosure is of a general nature and the non-limiting protocols below provide embodiments of the general disclosure.

Perfused Intestine Protocol

The ability to generate unequivocal data regarding the absorption of drug candidates in the human intestine, prior to clinical trials, is important in drug development. Such data can be generated using isolated intestinal segments because: (a) the drug candidates are presented via the intestinal lumen as in vivo; (b) the barriers between the intestinal lumen and blood are present and intact; and (c) the composition and flow characteristics of the perfusate mimic those in vivo.

Perfusion Conditions

Approximately three liters of perfusate are used per analysis. The perfusate preferably comprises matched human erythrocytes (preferably, previously washed) suspended in a buffer (at about 15 to about 20% (v/v)) comprising 4-6% human serum albumin, at a pH of preferably about 7.4.

Preferably, the perfusate is passed through a blood transfusion filter, followed by a leukocyte-removing filter, heparin is added and the pH adjusted, if necessary, to, preferably, about 7.4. The perfusate is preferably stored at room temperature until added to the perfusion apparatus. An aliquot of the surplus perfusate can be centrifuged (at about 1500 g for approximately 10 minutes at approximately 4° C.) to separate the plasma. The plasma can then be frozen at approximately −20° C. or lower for use as blanks in the analysis.

Intestine Samples and Perfusion

Isolated segments (about 30 cm to about 45 cm) of human intestine, immediately below the entry of the bile duct, for example, are preferably removed from hypothermic storage and used for each analysis.

The entire intestine sample is weighed and flushed with cold buffer via the mesenteric artery (or a branch thereof) for about 10 to about 15 minutes, at approximately 4-8° C., at a pH of approximately 7.4 and at a pressure of approximately 60-80 mmHg. This arterial buffer flush generally involves about 0.5 liter of buffer.

Following the arterial buffer flush is the equilibration period, wherein about 0.5 liter of oxygenated room temperature perfusate is passed through the intestine at a rate of approximately 20 ml/min. Approximately 0.5 liter of perfusate effluent is allowed to run to waste and the perfusion then switched to recirculating mode with 0.75 liter of oxygenated perfusate. The perfusion flow rate is preferably increased up to a target of about 90 to about 100 ml/min. over time without exceeding maximum pressure limits. The perfusate is recirculated until the intestinal core temperature is greater than about 35° C. and peristalsis is visible. The first pass and first recirculation combined generally last up to about 60 minutes.

At the end of the equilibration period, the perfusate is drained from the apparatus and replaced with about one liter of fresh oxygenated perfusate at about 37° C. in recirculation mode. This period is the stabilization period, which lasts for about 10 to about 15 minutes. Subsequently, perfusate aliquots are removed provided perfusion and physiological parameters, e.g., oxygen uptake, core temperature more than about 35° C., flow of about 90 ml/min. and pressure between about 60 to about 80 mmHg, are satisfied.

Dosing and Sample Collection

Preferred acceptance criteria for normothermic perfusion of human intestine prior to dosing with a test substance are:

| Perfusion & Physiological Parameters | |
| --- | --- |
| Arterial pressure (mmHg) | 40-60 |
| Arterial flow (ml/min.) | 200-300 |
| Portal pressure (mmHg) | 15-22 |
| Portal flow (ml/min.) | 600-800 |
| Venous PO$_2$ | >26 |
| Arterial PO$_2$ | >120 |
| pH | 7.3 ± 0.2 |
| Temperature (° C.) | 37.4 ± 2 |
| PCV (% cells) | 20-45% |
| Perfusion pressure (mmHg) | 60-80 |
| Perfusion flow rate (mesenteric artery) (ml/min.) | 90 |

The preferably labeled, e.g., radiolabeled, test substance (approximately 100 mg, approximately 100 µCi) and 3-5 preferably labeled internal standards, which are absorbed by passive diffusion at different rates, are administered, preferably as a pulse dose, in the same formulation in a maximum volume of about 15 ml into the lumen of the isolated intestine. This is designated "time zero."

The intestine is then perfused, in recirculating mode, for about 2 hours and aliquots (about 3 to about 5 ml) of the perfusate are removed at at least two of the following preferred times: pre-dosing and 5, 10, 15, 30, 45, 60, 90, 105 and 120 minutes post-dosing. Approximately half of each sample is frozen at about −70° C. and the remainder of each sample centrifuged and the plasma removed and frozen at about −70° C. Alternatively, in five milliliter samples, for example, about 1 milliliter is retained as whole perfusate and the remaining about 4 milliliters centrifuged and the plasma supernatant divided into four approximately equal aliquots for separate analyses.

At termination of the perfusion, the lumen of the intestine is washed with water and the washings retained, along with any remaining perfusate, for mass-balance analysis and/or metabolite profiling, if required. The intestinal segments are weighed, lumen contents are collected and weighed, and the lumen is flushed with about 100 milliliters of water and added to the intestinal contents and the combined mass recorded. The mixture is homogenized in a minimum amount of water and frozen for subsequent analysis, if desired, in approximately equal aliquots, such as about 40 milliliter aliquots. In addition, the perfusion apparatus is preferably rinsed with saline, water and/or alcohol. A sample of each rinse can be retained for subsequent analysis.

Embodiments of the perfusion method allow for multiple (single or cassette) dosing into sequential segments of the same intestine. In this preparation, the entire intestinal segment is perfused, as above, but after equilibration, the intestine (mesentery and lumen) is separated into three segments, preferably of approximately equal length, such that the lumen of each of the three segments is entirely separate, although the perfusate still circulates through each segment and subsequently mixes. One of the segments is then dosed with test substance and standards and aliquots of perfusate removed at timed intervals up to about one hour to about two hours post-dosing. This segment is then removed adjacent to the mesentery by, for example, cauterization, leaving the mesentery intact, but sealed. A liter of fresh perfusate is then flushed through the two remaining segments and the eluant collected in the first pass. Fresh perfusate (about 1 liter to about 1.5 liters) is then added and recirculated at a flow rate of ⅓ less than for 3 segments. The second segment is then dosed and the entire process repeated until all 3 segments have been dosed and aliquots of perfusate collected at timed intervals up to about one hour to about two hours post-dosing for each time zero.

Biopsies

Biopsies are preferably taken pre-dosing and at the termination of the perfusion and flash-frozen in liquid nitrogen at the point of collection prior to the homogenization. The biopsies can be subjected to histopathology and phenotyping for marker enzymes and other proteins.

Controls

Preferred controls include, but are not limited to, aliquots of perfusate and plasma collected pre-dosing, and, if possible, intestinal homogenates collected from a separate organ. Controls are preferably stored at about −80° C.

Analysis

Absorption of the test substance is determined by analyzing its rate of absorption from the intestinal lumen into the recirculating perfusate with time and comparing the rate with that of the internal standards. The raw data is generally in pmoles/ml, total pmoles and/or percent dose and includes the percent fraction for all absorbed compounds and the mass balance of labeled test substance in the perfusate, plasma, intestinal contents and intestinal wall. If radiolabeled compounds and standards are used, then total radioactivity measurements can be taken, and, if desired, HPLC profiling of the labeled test compound can be performed.

During perfusion, physiological parameters are monitored, such as arterial pressures and flows, organ core temperature, blood pH, active peristalsis and arterial and venous PO$_2$ and PCO$_2$; blood biochemistry parameters, such as electrolyte balance including, but not limited to, concentrations of potassium (mM), sodium (mM), chloride (mM), calcium (mM), albumin (g/dl), ALP (alkaline phosphatase) (µ/l), ALT (alanine transaminase) (µ/l), amylase (µ/l), AST (aspartate transaminase) (µ/l), GGT (gamma glutamyl transferase) (µ/l), Cal (mg/dl) and BUN (blood urea nitrogen) (mg/dl); biomarkers, such as, glucose (mg/dl) utilization and lactate (mM) production; absorption of internal standards, such as $^3$H-mannitol (target concentration about 100 µCi; target dose about 20 µM), antipyrine (target dose about 20 µM), terbutaline (target dose about 20 µM), dextran (about 10 to about 70 kD) and/or other labeled or unlabeled standards; and presence and characteristics of the test compound and/or metabolites in bile, perfusate and liver.

Applications of Perfused Intestine Model in Drug Development

Perfusion studies can be used in numerous phases in drug development. For example, absorption studies can be used in assessing single pulse doses and/or repeated doses of a drug candidate, constant infusion, cassette dosing, effects of formulation, regional differences, effects of food and saturation kinetics, for example. Metabolic studies can be used to assess metabolite identification, metabolite quantification, saturation kinetics and regional differences, for example. Distribution studies can be used to assess covalent binding, for example.

Perfused Liver Protocol

Species, strain and gender differences in drug metabolism have been well documented over the last 50 years. In many cases, these differences are attributed to variations in the concentration of intracellular enzymes and cofactors, particularly in the liver. In drug development, the appearance of either new metabolites or vastly different concentrations of particular metabolites from that found in initial studies of a drug candidate can lead to a considerable amount of additional resources and lost time.

Currently, attempts to predict human liver metabolism are performed with data from in vitro preparations, i.e., tissue slices, isolated hepatocytes, S9 fractions or microsomes. Although these studies are important, they sometimes: (a) do not mimic metabolism in the whole liver; (b) identify potential rather than actual metabolism; and (c) give no measure of subsequent partitioning of metabolites between blood and bile, and thus the exposure of extra-hepatic organs and tissues to the biproducts of liver metabolism.

In isolated vascular perfused human liver studies, these shortcomings may be avoided. Instead, test substances and validation standards may be delivered via matched blood-based perfusate at physiological flow rates to a stable, viable hepatic tissue or organ with normal biliary secretory mechanisms. Consequently, this model is ideally suited to determine the nature and extent of drug uptake, drug metabolism and drug clearance in human liver, as well as biliary elimination, mass-balance and measurements of the subsequent partitioning of metabolites between blood and bile. In addition, specific metabolites may be characterized in separate studies.

Exemplary Perfusion Conditions

Approximately five to six liters of perfusate are used per analysis. Fresh perfusate containing human erythrocytes (previously washed and centrifuged) is suspended in buffer containing 6% human serum albumin (at about room temperature, about 15 to about 20% v/v, pH about 7.4). If the test compound is known to bind to α-1-glycoprotein, then 4% human serum albumin is used instead of 6% or 2% human serum albumin is used with 2% α-1-glycoprotein. The perfusate is then passed through a Pall 40 micron blood transfusion filter, followed by a "leukocyte-removing" filter, approximately 15 N.I.H. units/ml of heparin are added and the pH adjusted, if necessary, to approximately 7.4 using, for example, $NaHCO_3$. The perfusate is preferably stored at room temperature until added to the perfusion apparatus. An aliquot of the surplus perfusate, such as approximately 50 ml, may be centrifuged (approximately 1500 g for approximately 10 minutes at approximately 4° C.) to separate the plasma and blood cells. This plasma may be frozen at approximately −20° C. or lower for use as blanks in the analysis.

Throughout the perfusion, the flow, pressure and temperature are recorded in both perfusion circuits. The $PO_2/PCO_2$ is measured at approximately 15 minute intervals in the inlets via the hepatic artery and portal vein and in the outlet via the vena cava. Each liver is allowed an equilibration period of about 45 to about 60 minutes and bile is collected in pre-weighed containers. Only satisfactory preparations, in terms of perfusate flow and pressure and bile flow are dosed with test substances.

Supplementary bile salts are added initially to the perfusate and then throughout the perfusion period. Bile salts include, but are not limited to, about 1 gram of sodium glycocholate hydrate (Sigma G7132), about 0.5 gram sodium glycodeoxychoate (Sigma G9910) and sodium glychochenodeoxycholate (Sigma G0795) dissolved in 25% hydroxypropyl beta cyclodextrin (HPβCD), wherein the total mass of bile salt in the HPβCD solution is 20 g. About 1 gram of bile salt HPβCD solution per liter of perfusate is preferred initially, followed by about 1 gram of solution into the perfusate at 1, 2, 3, 4 and 5 hours. Thus, the perfusate will be comprised of washed matched human erythrocytes suspended in human plasma supplemented with bile salts.

Perfused Liver Samples

An isolated human liver is removed from hypothermic storage and, if possible, the hepatic artery, portal vein and vena cava are cannulated. The liver is then flushed at about room temperature with about one liter to about two liters of cold buffer, such as Krebs-Ringer bicarbonate buffer (pH approximately 7.4), under gravity, for about 10 to about 15 minutes, to remove the transport/storage medium.

About 1.5 liters of fresh perfusate containing human erythrocytes (previously washed) suspended in buffer containing 2%, 4% or 6% human serum albumin, as described above, at about room temperature, about 15 to about 20% v/v, pH about 7.4, are then pumped at approximately 20 ml/min. into the hepatic artery and portal vein and allowed to recirculate for about 45 to about 60 minutes in an equilibration phase.

After approximately 1 liter has run to waste, about two liters of fresh perfusate are recirculated within the perfusion apparatus. The temperature of the perfusate is raised to about 37° C. and perfusion flow rates are increased to target flow rates, e.g., about 200 to about 300 ml/min. through the hepatic artery and about 400 to about 800 ml/min., preferably about 600 ml/min., through the portal vein for about 10 to about 15 minutes in a stabilization phase.

Dosing and Sample Collection

The solubility and stability of the test compound are preferably confirmed prior to the perfusion study as described above. Once the perfusion preparations are stable with respect to perfusate flow and pressure, the test substance is added to the recirculating perfusate. Preferred acceptance criteria for normothermic perfusion of human liver prior to dosing with a test substance are:

| Perfusion & Physiological Parameters | |
| --- | --- |
| Arterial pressure (mmHg) | 40-60 |
| Arterial flow (ml/min.) | 200-300 |
| Portal pressure (mmHg) | 15-22 |
| Portal flow (ml/min.) | 600-800 |
| Venous $PO_2$ | >26 |
| Arterial $PO_2$ | >120 |
| pH | 7.3 ± 0.2 |
| Temperature (° C.) | 36.5 ± 2 |
| PCV (% cells) | 15-20% |
| Perfusion pressure (mmHg) | 60-80 |
| Perfusion flow rate (mesenteric artery) (ml/min.) | 90 |

The dosing vehicle is, preferably, DMSO at a final concentration of about 0.1% v/v in perfusate. The preferred dosing regime comprises adding about 50 mg of, preferably, labeled, such as radiolabeled, test compound or a mixture of non-labeled and labeled, such as radiolabeled, test compounds, in DMSO as an infusion into the perfusate over a period of time (median Tmax=about 1 hour). If radiolabels are used, the target radioactive dose is preferably about 100 μCi per liver.

Each dosing solution is preferably put into a pre-weighed syringe with an attached cannula and the syringe is reweighed. The contents of the syringe are expelled as a pulse dose into the perfusate. The test compound is added at designated "time zero" and the liver perfused for about 240 minutes. A standard, such as tetra-BSP (about 20 μM), is added at the end of the about 240 minutes and the liver is perfused for about 120 minutes more. The liver is perfused for about six hours in total. Perfusate samples (about 10 ml per sample) are collected, for example, at at least two of the following times during perfusion: pre-dose and 5, 10, 15, 30, 45, 75, 105, 135, 165, 195, 225 and 239 minutes post-dose.

In addition, bile is continuously collected throughout the perfusion, for example, at at least two of the following times: pre-dose and 30, 60, 90, 120, 150, 180, 210 and 240 minutes post-dose.

The liver is dosed with at least one positive control at about four hours after "time zero" and the perfusate sampled, for example, at at least two of the following times: 245, 150, 255, 270, 285, 300, 330 and 360 minutes past time zero.

In each about 10 ml sample, about 1 milliliter is retained as whole perfusate and the remaining about 9 milliliters centrifuged and the plasma supernatant divided into four approximately equal aliquots. The supernatants and bile samples can be stored at about −80° C. until analyzed for dosed test compound and any metabolites. Following sampling of each about 10 ml aliquot, about 10 ml of control perfusate (perfusate without the test substance) is added to the perfusion system.

At perfusion termination, all the remaining perfusate and apparatus washings are collected for mass-balance analysis and/or metabolite profiling, if desired (in perfusate/plasma). The gall bladder, if not dissected from the liver prior to the perfusion, can be homogenized and assayed for total radioactivity, assuming the test compound is radiolabeled.

After the tissue is collected, the perfusion apparatus is preferably rinsed with saline and, at the end of the perfusion, with water and alcohol. A sample of each rinse is preferably retained for analysis. In addition, the dosing syringe and cannula are reweighed after dosing and washed with water and methanol. The syringe/cannula washing is assayed for radioactivity, if applicable, or other label, if applicable. The test compound dose administered is calculated by subtracting the syringe washings from the total amount of radioactivity, for example, taken-up into the syringe/cannula.

Biopsies

Biopsies are preferably taken pre-dose and at 360 minutes post-dose and flash-frozen in liquid nitrogen at the point of collection. The remainder of the liver is homogenized at the end of the perfusion. The biopsies can be subjected to histopathology and phenotyping for marker enzymes and other proteins.

Controls

Preferred control samples include, but are not limited to, aliquots of bile, perfusate and plasma collected pre-dose, and, if possible, liver homogenates collected. from a separate organ. All samples are preferably stored at about −80° C.

Analysis

If radiolabeled compounds and standards are used, then total radioactivity measurements can be taken, and, if desired, extraction and HPLC profiling of the labeled test compound and/or metabolites can be performed. In addition, possible structural identification may be performed on metabolites and extraction and analysis of the standard, such as tetra-BSP and its glutathione conjugates in plasma and bile, can be conducted.

During perfusion, physiological parameters may be monitored, such as arterial pressure and flow, organ core temperature, blood pH and arterial and venous $PO_2$ and $PCO_2$; blood biochemistry parameters such as electrolytes including, but not limited to, potassium (mM), sodium (mM), chloride (mM), calcium (mM), albumin (g/dl), ALP (μ/l), ALT (μ/l), amylase (μ/l), AST (μ/l), GGT (μ/l), Cal (mg/dl), bile rubin (μ/l) and BUN (mg/dl); biomarkers such as glucose (mg/dl) utilization and lactate (mM) production; absorption of standards such as $^3$H-mannitol, antipyrine, propanalol, atenolol, bromosulphophthalein (tetra-BSP), 1-naphthol, 7-ethoxycoumarin, terbutaline and/or other labeled or unlabeled standards; and presence and characteristics of the test compound and/or metabolite(s) in bile, perfusate and liver.

Applications of Perfused Liver Model in Drug Development

Perfusion studies can be used in numerous phases in drug development. For example, first pass clearance and/or plasma clearance studies can be used to assess a test compound's half-life, single pulse dosing, repeated pulse dosing, plasma steady state and cassette dosing. Biliary excretion can be used to quantify the parent drug (substance being tested) or to assess saturation kinetics, for example. Metabolic studies can be used to assess metabolite identification, metabolite quantification, partitioning of metabolites between plasma and bile and saturation kinetics, for example. Distribution studies can be used to assess tissue clearance and covalent binding, for example. Absorption, distribution, metabolism and/or excretion studies can be used to study hepatic diseases.

Perfused Kidney Protocol

The ability to determine qualitatively and quantitatively the fates and effects of drug candidates in human kidneys, prior to clinical trials, is important in drug development. Processes of particular relevance to drug development include, but are not limited to: (a) renal clearance, plasma clearance, and glomerular filtration rate—urine is the principle route of drug elimination and the kidneys are a major site for drug-drug interactions; (b) metabolism—the kidneys have significant Phase I and Phase II drug metabolizing activities such as determining percent tubular reabsorption or active secretion; and (c) distribution—the partitioning of metabolites formed in the kidneys between blood and urine can dictate the subsequent exposure of other organs to pharmacologically active or toxic metabolites.

As with all human organs, the validation process for isolated perfused human kidneys (IPHK) is designed for both hypothermic preservation perfusion after excision of the kidney from the donor and normothermic physiological perfusion for drug research and development.

Preferably, prior to any drug candidate testing using IPHK, as much as possible is known about the history of each kidney in the test and, more importantly, its current condition compared with a database of hundreds of kidneys that were successfully transplanted and those that were not. This is the mechanism by which kidneys are accepted for drug research and the rationale for each decision is recorded.

Perfusion Conditions

Donated kidneys are transferred to hypothermic storage as soon as possible after collection and perfused with a buffer, such as KPS-1® buffer (Organ Recovery Systems, Inc., Des Plaines, Ill.), at about 6 to about 8° C. for a minimum of about 4 hours.

The kidney(s) is then flushed with about 1 liter of fresh perfusate and the temperature of the perfusate effluent raised to about 37° C. When the kidney(s) is stable with respect to perfusion pressure and flow and urine formation, the first perfusate is replaced with about 1.5 liters of fresh perfusate.

In embodiments, the perfusate used for kidney perfusions is derived from a liver perfusion experiment in which a test compound has been perfused through a human liver. In this way the renal handling and/or further metabolism of hepatic metabolites can be resolved.

Dosing and Sample Collection

Preferred acceptance criteria for normothermic perfusion of human kidneys prior to dosing with a test substance are:

| Perfusion & Physiological Parameters | |
|---|---|
| Perfusion pressure (mmHg) | ≤80 |
| Perfusate flow rate (ml/min.) | 250-450 |
| PH | 7.4 ± 0.3 |
| Temperature (° C.) | 36.5 ± 2 |

-continued

| Perfusion & Physiological Parameters | |
| --- | --- |
| Glomerular filtration rate (GFR) (ml/min.) | 20-80 |
| Arterial pressure (mmHg) | 40-60 |
| Arterial flow (ml/min.) | 350-450 |
| Venous PO$_2$/PCO$_2$ | 20-50/5-30 |
| Arterial PO$_2$/PCO$_2$ | 120-140/5-30 |
| PCV (% cells) | 16-22 |

The test compound and internal standards are dosed directly into the perfusate and aliquots of perfusate (about 3 ml to about 5 ml) are taken about every 15 minutes and urine collected batchwise about every 15 minutes for about 2 hours. Each perfusate sample is subdivided into four approximately equal aliquots. Two aliquots are retained for analysis and the other two centrifuged and the plasma removed and stored frozen at about −70° C. until analyzed. Urine samples are collected into tarred tubes, weighed and frozen at about −70° C. for subsequent analysis of, for example, test compounds and metabolites.

After the test compound has been administered to an IPHK for sufficient time, for example, about 60 minutes, exogenous positive controls can be added to the circulating perfusate to validate those critical processes not covered by endogenous compounds, i.e., the internal standards. These additional, preferably labeled, controls include, but are not limited to, p-amino hippuric acid (for assessing tubular secretion) and a glutathione conjugate (for assessing the integrity of the mercapturic acid pathway).

Perfusate and urine samples are collected about every 30 minutes for a further about 2 hours after dosing the positive controls and are retained for analysis, which includes, but is not limited to, measuring physiological parameters; measuring blood chemistry parameters, such as potassium (mM), sodium (mM), chloride (mM), calcium (mM), glucose (mg/dl), lactate (mM), albumin (g/dl), ALP (μ/l), ALT (μ/l), amylase (μ/l), VAG (μ/l), AST (μ/l), 2-GST (glutathione S-transferase) (μ/l), creatinine (mg/dl) and urinary excretions (μ/l); measuring test compounds and/or metabolites in urine, perfusate and kidney; and measuring parameters of urine biochemistry, such as N-acetylglucosaminidase, glutathione S-transferase and proteins and peptides.

Applications of Perfused Kidney Model in Drug Development

Perfusion studies can be used in numerous phases in drug development. For example, plasma clearance studies can be used to assess single pulse dosing, repeated pulse dosing, single compound dosing, plasma steady state, cassette dosing and saturation kinetics. Renal excretion can be used to assess GFR, test compound percent reabsorbed, test compound percent secreted and saturation kinetics, for example. Metabolic studies can be used to assess metabolite identification, metabolite quantification, partitioning of metabolites between plasma and urine and saturation kinetics, for example. Distribution studies can be used to assess regional distribution and covalent binding, for example.

Perfused Human Lung Protocol

The isolated perfused human lung preparation (IPHLung) is a versatile system for studying lung specific drug-related activities including, but not limited to, assessing inhaled drug performance by quantitating ventilatory function, drug preparation stability, drug absorption via the airways, drug uptake from the blood, drug metabolism, clearance and retention, extent of edema, pharmacological effects, drug efficacy, drug toxicity and drug-drug interactions, as well as assessing physiologic function and pharmacologic responsiveness of the lungs by inducing bronchoconstriction followed by introducing salbutamol, or other internal standard, using nebulized delivery. Reliable quantification of one or more of these activities can provide the basis for key decision making in drug candidate selection and/or problem solving, if necessary, after test compounds are released into the market.

Moreover, perfusion studies overcome numerous problems of in vitro lung studies, including, but not limited to, allowing for the over 40 cell types in the lung, many of which cannot be isolated and many of which change their phenotype when cultured.

Perfusion Conditions

Preferably, a pair of respiring lungs is flushed free of donor blood with about 2 liters of buffer, such as Krebs-Ringer buffer, at about 6 to about 8° C. at about 12 to about 18 ml/min. The lungs are then perfused via the pulmonary artery with fresh perfusate with a pressure of less than about 18 mmHg and the flow continuously recorded. The effluent from the pulmonary veins can be recirculated (except under first-pass conditions). About two liters of perfusate are used for the perfusion study.

Preferred biomarkers are enzymatic, including, but not limited to, angiotensin converting enzyme. Preferred internal standards include, but are not limited to, about 1 mg/ml salbutamol or other bronchodilator (dose of about 150 μg), about 1 mg/ml ipatropium (dose of about 150 μg) and polyamines.

Dosing and Sample Collection

Preferred acceptance criteria for normothermic perfusion of human lungs prior to dosing with a test substance are:

| Perfusion & Physiological Parameters | |
| --- | --- |
| Perfusion pressure (mmHg) | ≥18 |
| Perfusate flow rate (ml/min.) | 250-450 |
| pH | 7.4 ± 0.3 |
| Temperature (° C.) | 37.0 ± 1 |
| Airflow (l/min.) | at least 66 |
| Nebulizer-tidal volume (ml) | 400-500 |
| Compliance Curves | @ about 30 minute intervals |

Pre-dose and at other sample times, perfusate samples are taken and blood chemistry is assessed in terms of, for example, pH, pCO$_2$, lactate and inorganic ions. In addition, samples are taken at the same times to assess angiotensin converting enzyme release.

After dosing of the test compound or cassette of compounds (via the airway using a nebulizer or into the perfusate) at a concentration of about 0.3 to about 1.0 mg/ml (dosage of about 45 to about 150 μg) (referred to as "time zero"), aliquots (preferably about 3 to about 5 ml) of perfusate are removed pre-dose and at at least two of the following times: 5, 10, 15, 30, 45, 60, 90 and 120 minutes post-dose for absorption studies, for example. About 1 ml of each aliquot is retained for blood chemistry and hematocrit measurements. A portion of the remaining aliquot is set aside (about 1 ml whole perfusate) and the remainder is centrifuged and the resulting cell-free supernatant further divided into aliquots (at least about 2 ml each), which are flash frozen in liquid nitrogen at the point of collection.

After about 120 minutes post-dose, the perfusate is replaced with fresh perfusate, which is circulated for about 30 minutes. Perfusate samples (about 3 to about 5 ml aliquots) are taken at, for example, 5, 10, 15 and 30 minutes from the beginning of the fresh perfusate circulation. About 1 ml of each aliquot is retained for blood chemistry and hematocrit measurements. A portion of the remaining aliquot is set aside (about 1 ml whole perfusate) and the remainder is centrifuged and the resulting cell-free supernatant further divided into aliquots (at least about 2 ml each), which are flash frozen in liquid nitrogen at the point of collection.

At the end of the 30 minutes, metabolic markers are added to the perfusate and the perfusate is again sampled at, for example, 5, 15, 30 and 60 minutes (to the end of the perfusion and/or at other time points, if feasible) after metabolic marker addition in about 3 to about 5 ml aliquots, which are subsequently frozen for later analysis of the disposition/metabolism study results. About 1 ml samples of plasma are also taken at, for example, 5, 15, 30 and 60 minutes (and other time points as feasible) after metabolic marker addition for polyamine uptake determination. Markers include, but are not limited to, probes added to the perfusate, ethoxycoumarin (CYP1A) at a dose of about 20 µM, and 1-naphthol (glucuronidation and sulfation) at a dose of about 10 µM.

At about three hours and 30 minutes from time zero, histamine, or other bronchoconstrictor or vasodilator, is added to the perfusate at a concentration of about $10^{-5}$ M to about $10^{-6}$ M for a pharmacology study. About ten minutes later, bronchoconstriction is assessed. If evidence of bronchoconstriction is not found, then histamine is again added, but at an increased concentration of about $10^{-6}$ M to about $10^{-7}$ M, respectively. Increased concentrations of histamine are added to the perfusate every ten minutes until evidence of bronchoconstriction is apparent at which time inhalation of a control, such as salbutamol, is initiated at a dosage of 2×150 µg from 1 mg/ml stock solution. Preferably inhalation is performed using a ProDose device with a 150 µl disk. The presence of bronchodilation is determined over about 15 minutes. Papaverine or other vasodilator is then added to the perfusate at a concentration of about $10^{-7}$ M and the presence of bronchodilation determined.

Biopsies

Histology studies can be performed on each lung using a container, such as a 500 ml plastic screw-top container, filled with neutral buffered formalin, for example. The lung lobe that can be most easily isolated from the remaining lung is removed with the entire length of the bronchus, avoiding damage to the parenchymal tissue. A ligature is loosely placed around the bronchus. The bronchus can be held with forceps and a syringe used to slowly insufflate the entire lung lobe with formalin. Insufflation is discontinued after the lobe is expanded 75%. The bronchus is ligated and the lobe placed in the formalin. The date and time of this initial fixation is noted on the container.

Applications of Perfused Lung Model in Drug Development

Perfusion studies can be used in numerous phases in drug development. For example, absorption studies (via the airways) can be used to assess formulations of the test compound, such as liquid, dry powder or nebulizer (tidal volume), and dosing mechanisms, such as single dosing, repeat dosing or cassette dosing. Plasma clearance studies can be used to assess single pulse dosing, repeated pulse dosing, single compound dosing, cassette dosing and constant infusion dosing, for example. Metabolic studies can be used to assess metabolite identification, metabolite quantification, volatile metabolites and saturation kinetics, for example. Distribution studies can be used to assess accumulation of the test compound in tissues, residence times and transit times, for example.

Safety/Toxicity Testing

1. Hepatotoxicity

There are five commonly used whole cell preparations for the study of hepatic functions and toxicity: primary hepatocytes, hepatocytes in culture, liver slices, perfused livers and livers in vivo. Each of these methods has advantages and disadvantages that should be taken into account when designing experiments to determine the fates and effects of drug candidates in vivo. In practice this has proven to be a difficult standard to meet. For example, references to major advantages attributed to the use of isolated hepatocytes in drug research always include "convenience" and the "large quantity" of data generated from a single liver. However, when "quality" of data is paramount, i.e., when making drug development decisions, this in vivo model suffers from a loss of lobular architecture, regional distribution of enzymes is disrupted, the cells have diminished activity of many enzymes and important non-parenchymal cells are absent. Similarly, in cultured hepatocytes, many enzyme systems revert to fetal states and cytochrome P450 content declines limiting their use in toxicity and drug metabolism studies. However, these methods remain widely used in the absence of alternatives.

In contrast to primary or cultured hepatocytes, liver slices retain lobular architecture, however cells in this form leak potassium and most importantly do not produce bile, a major route for clearing potential toxins (endogenous and exogenous) from the liver.

Perfused liver systems simulate in vivo conditions more than any of the techniques above. Normal hepatic architecture, microcirculation and bile production are maintained. Compounds, free and protein-bound, are delivered to all cell types via the blood (cells and plasma) at the same flow rates and perfusion pressures operating in vivo. Moreover, in assessing drug candidates for hepatotoxicity, the fact that the numerous cell types in perfused livers are less compromised, results in fewer false positives and false negatives and better pharmacokinetic/toxicity correlations.

A. Perfusion Conditions

Donated human livers are perfused as described above. Test compound(s) are added to the perfusate as (a) a pulse dose, (b) repeated pulse doses, (c) constant infusion or (d) rising plasma concentrations. Perfusate and bile samples are collected every about 15-30 minutes over about 4-8 hours and analyzed for markers of hepatic/biliary damage in addition to drug/metabolite concentrations. In one embodiment, liver biopsies are taken every hour and flash frozen in liquid nitrogen at the point of collection as described above.

B. Markers of Toxicity and Positive Controls

| Target Syndrome | Method of Diagnosis & Histochemistry |
| --- | --- |
| Fatty liver formation | Inhibition of carrier protein synthesis |
| Cholestasis | Biliary excretion |
| Necrosis | Proteomics |
| Apoptosis | Proteomics imaging |
| Ischemia/Reperfusion Injury | Protein adducts |
| Genotoxicity | DNA-adducts |
| Enhanced Portal Pressure | Direct |
| Induction/Repression | Microarrays |
| Detoxication Pathways | Activation/Inhibition |

Collectively this battery of assays records the effects of drugs and/or metabolites, at clinically relevant concentrations in blood, on some of the key liver functions including: transport processes in and out of the liver, transcription-translation-post translational modification and exocytosis of proteins and conjugated proteins, cytokine production, stimulation of apoptosis or necrosis, free radical generation, DNA-adduct formation, and induction or inhibition of detoxication pathways.

2. Nephrotoxicity

As a vital organ, the kidney performs many unique functions that can be monitored for evidence of impairment when exposed to drug candidates. These functions include: regulation of the body's fluid volume (a major contributor to the control of blood pressure); regulating the pH of the body in concert with lungs through the excretion of fixed, non volatile acids and the conservation of base; excretion of waste products and the conservation of critical body constituents, e.g., electrolytes, substrates etc.; detoxification of certain drugs; and synthesis and release of hormones, such as rennin and erythropoetin, and the conversion of vitamin $D_3$ to the 1,2-dihydroxy form.

To carry out these functions, the integration of many physiological and biochemical actions of the kidney is required. Analysis of these functions provides a means of assessing the inherent risk of drug candidates for drug-induced renal damage.

A. Perfusion Conditions

Donated kidneys are subjected to hypothermic perfusion, flushed and stabilized with perfusate at about 37° C. and perfused with about 1 to about 1.5 liters of fresh perfusate as described above.

Test compound(s) are added to the perfusate as (a) a pulse dose, (b) repeated pulse doses, (c) constant infusion or (d) rising plasma concentrations. Perfusate and urine samples are collected about every 15-30 minutes over about 2-4 hours during perfusion and analyzed for markers of renal damage in addition to drug/metabolite concentrations.

C. Markers of Toxicity and Positive Controls

| Target Syndrome | Positive Controls | Method of Diagnosis |
| --- | --- | --- |
| Acute renal failure | Gentamycin Cisplatin | Proteomics |
| Pre renal azotaemia due to impaired perfusion | ACE inhibitors Cyclosporins | Renal haemodynamics |
| Acute intestinal nephritis | Allopurinol Sulphonamides | Markers of inflammation |
| Obstructive nephropathy | Methotrexate Acyclovir | Urine flow GFR |

3. Cardiac Toxicity

A. Perfusion Conditions

After preservation, isolated hearts are removed from cold storage and perfused, in the standard Langendorff format with a buffer, such as RS1 comprising washed matched human erythrocytes (about 15 to about 20% v/v), human serum albumin (about 4% w/v) at a pH of about 7.3±2 and a temperature of about 37° C. In one embodiment, human serum albumin is replaced with human plasma.

$PO_2$ (about 150 to about 250 mmHg) and $PCO_2$ (about 25 to about 35 mmHg) are maintained and electrolyte concentrations adjusted to normal values in blood. Once the organ is stable with respect to perfusate pressure and flow, heart rate and developed left ventricular pressure (DLVP) (dP/dt) and a pre-dose sample has been removed, test compound(s) are added to the perfusate as (a) a pulse dose, (b) repeated pulse doses, (c) constant infusion or (d) rising dose infusion. Blood chemistry/biochemistry markers including, but not limited to, electrolytes, glucose, $PO_2$ A-V difference, $PCO_2$ A-V difference, troponin-1 and albumin conjugates are measured.

B. Markers of Toxicity and Positive Controls

| Target Syndrome | Method of Diagnosis |
| --- | --- |
| Langendroff properties | Pressure |
|  | Flow |
|  | Heart rate |
| Re-animation interventions | Defibrillation Pacing Isotopes |
| Work Capacity | dP/dt |
| Diastolic | End diastolic pressure-volume ratio |
| Endothelial function | Coronary flow reserve |
| Disruption of cellular function | Proteomics |
| Apoptosis | Caspase 3 |
| Necrosis | Troponin-1 |
| Ischemia | Albumin adducts |

Target Diseases

Specific organs and diseases are summarized below although each disease may be divided into distinctive phases depending on the stage of disease in each donated organ.

| Disease | Organs |
| --- | --- |
| Cancers | Liver, lung, kidney, colon, pancreas, bone, lymph nodes |
| Diabetes | Liver, kidney |
| Infections | Liver, kidney, lung, intestine |
| Metabolic | Heart, liver, kidney |
| Ischaemia/Reperfusion injury | Liver, kidney, heart, intestine |
| Vascular | Arteries, veins |
| Organ rejection post-transplant | Liver, kidney, pancreas |

In the practice of the methods of this invention, devices and apparatus for perfusing organs for transplant can be used, as disclosed in co-owned U.S. Pat. No. 6,673,594 and U.S. published patent application No. 2004/0224298, each of which is expressly incorporated by reference in its entirety herein. However, one of ordinary skill in the art will recognize that there are differences in the way organs are used according to the inventive methods and the way organs are maintained by perfusion for organ transplantation. These may include, but are not limited to, the following in ex vivo perfusion: use of matched human erythrocytes; use of about 2% to about 6% w/v human serum albumin in perfusate or whole plasma; perfusate temperature of about 37° C.; oxygenation of perfusate using compressed air (all organs); perfusion at physiological flow rates and pressures for each organ; added chemicals in perfusate, e.g., N-acetylcysteine (about 0.23 g/l), ATP (about 0.01 g/l), dibutylcyclic AMP (about 0.01 g/l), superoxide dismutase (about 0.33 ml/l), secretin (about 7 μl/l for liver perfusions), glycocholic acid (about 0.13 g/3 l for liver perfusions), dexamethasone (about 471 μg/l for intestinal perfusions), noradrenaline infusion (about 72 μg/hr for intestinal perfusions) and mixtures of essential and non-essential amino acids (for kidney perfusions); organs perfused first-pass or in recirculating mode; human lungs ventilated by positive or negative pressure; and use of organ-specific positive and negative controls.

EXAMPLES

The Examples that follow are illustrative of specific embodiments of aspects of the invention.

Example 1—Preparation of Perfusates

Perfusates are prepared according to the following protocol:

(i) 5 liters of Krebs-Ringer buffer are made and the pH adjusted to 7.4 before use, with HCl or NaOH;

(ii) 5,000 units of heparin are added per liter of Krebs-Ringer buffer;
(iii) Perfusates comprising heparin and non-heparin containing Krebs-Ringer buffer are refrigerated at 4-8° C. or on ice before use;
(iv) Matched red blood cells (RBCs; 4 units) are removed from refrigeration (Blood Type O or AB RBCs are used if donor-matched cells are not available, as appropriate);
(v) Packed cells are pooled in a 2 liter beaker (or appropriate alternative) and mixed gently by swirling;
(vi) Cold Krebs-Ringer buffer containing heparin (5,000 units per liter of buffer) is then added, so that the volume of cells increases by ~50%, and the cells mixed with heparinized buffer by swirling;
(vii) The suspended cells are divided into large centrifuge bottles, preferably only filling the bottles ⅔ full to achieve optimum separation. The bottles are balanced and centrifuged for 20 minutes at ~4° C. at 1500 g (3,400 rpm) and the supernatant and buffy coat removed by aspiration;
(viii) The packed cells are resuspended with any remaining buffer containing heparin and topped with Krebs-Ringer buffer without heparin as necessary, with the remainder of the heparin-containing buffer divided between each aliquot of cells, with the centrifuge bottles being topped to ⅔ full with Krebs-Ringer buffer without heparin. The cells are mixed with buffer by gentle inversion and without shaking. The cell suspension is then centrifuged as above and the buffy coat removed;
(ix) The washing steps are repeated using Krebs-Ringer buffer without heparin once or twice or until the supernatant is clear. The contents of the packed cell volumes are combined when necessary and centrifugation time adjusted to up to 25 minutes when cells do not pellet efficiently;
(x) Once the supernatant is clear (and has been aspirated), the washed cells are pooled into a pre-weighed beaker (2 liter capacity) and the cell mass recorded;
(xi) RS1 buffer (2 liters) is prepared by diluting RS1 concentrate (~1400 g) with sterile water and buffering with NaHCO₃ (2.1 g per liter), the pH adjusted to between 7.2 to 7.4 with NaOH or HCl as needed, and then 10 vials of human albumin are added and the pH adjusted if necessary to 7.4. The total mass of the RS1/HSA buffer is 2000 g, which is then filtered through a 0.2 micron sterile filtration unit and stored refrigerated until blood cell washing is complete;
(xii) The washed cells are then mixed with an amount of RS1/HSA buffer equal to three times the mass of cells, e.g., 600 ml of cells plus 1800 ml of RS1/HSA buffer, and gently, but thoroughly, mixed by swirling. Duplicate samples are removed and the hematocrit tested, and adjusted if necessary with gentle mixing to a final value of about 10 to about 30%, preferably about 20%;
(xiii) A peristaltic pump is used to filter the resulting cell suspension through a 20-60 micron, preferably 40 micron, Pall transfusion filter to remove any residual clots and then through the Pall leukocyte filter under gravity. The filtered perfusate is then divided into the appropriate amount depending on the organ, the perfusate being kept refrigerated until use, but then warmed to room temperature before use with the organ or tissue. Prior to use and after warming, the pH is checked and adjusted to about 7.4 (7.2-7.6) immediately before use using a saturated solution of NaHCO₃ or concentrated HCl diluted with saline.

Organ-specific additions to the above perfusate were prepared as follows:

| Organ | Chemical | Amount Range | Preferred Amount |
|---|---|---|---|
| Liver | N-acetylcysteine | 37-150 mg/l | 75 mg/l |
|  | ATP | 5-20 mg/l | 10 mg/l |
|  | Dibutylcyclic AMP | 12-50 µM | 25 µM |
|  | Superoxide dismutase | 1-4 µg (in 5% acid) | 2 µg (in 5% acid) |
|  | Glycocholic acid | 50-200 µM | 100 µM |
|  | Glycochenodeoxycholic acid | 25-100 µM | 50 µM |
|  | ³H-mannitol | 50-200 µg (if required) | 100 µg (if required) |
| Intestine | Noradrenaline | 1-5 µl/l | 2.25 µl/l |
|  | Dexamethasone | 1-4.5 mg/l | 2.2 ml/l |
| Kidney | Methionine | 37-150 mg/l | 74.6 mg/l |
|  | Alanine | 89-160 mg/l | 178.2 mg/l |
|  | Glycine | 75-300 mg/l | 150.1 mg/l |
|  | Serine | 105-420 mg/l | 210.2 mg/l |
|  | Proline | 115-260 mg/l | 230.2 mg/l |
|  | Isoleucine | 65-262 mg/l | 131.2 mg/l |
|  | Mannitol | 0.5-2 g/l | 1 g/l |
|  | Creatinine | 7-27 mg/l | 14.61 mg/l |
|  | N-acetylcysteine | 0.35-1.4 g/l | 0.7 g/l |
|  | ATP | 0.01-0.06 g/l | 0.03 g/l |
|  | Dibutylcyclic AMP | 0.01-0.06 g/l | 0.03 g/l |

Example 2—Human Liver Toxicity of Acetaminophen

The primary purpose of this protocol is to assess metabolism and binding of the well known hepatotoxin [¹⁴C] acetaminophen.

Preparation of Normothermic Perfusate

Matched human erythrocytes are washed five times in an equal volume of OPB-1 buffer (pH 7.4) with intermediate centrifugation. After the final centrifugation, the packed cells are resuspended in OPB-1 buffer at pH 7.4 containing 4% albumin (filtered through a 0.45 micron and 0.2 micron filter) such that the packed cell volume is approximately 15%-20% (v/v) of the final resuspended volume. The perfusate is passed through a Pall leukocyte filter and heparin (15 N.I.H. units/ml) added, and the pH adjusted, if necessary to pH 7.4 using NaHCO₃. The perfusate is stored at room temperature until added to the perfusion apparatus (2×2 liters/perfusion). An aliquot of the surplus perfusate (50 ml) is centrifuged (~1500×g for 10 minutes at 4° C.) to separate the plasma and blood cells. The plasma is frozen at ~70° C. and kept for use as blanks in the analysis.

Perfusion Conditions

Each liver is removed from hypothermic storage and flushed (first pass) with OPB-1 buffer via the hepatic artery (1 liter) and portal vein (1 liter) to remove endogenous metabolites, tissue debris, etc. from the vascular bed. The liver is attached to the perfusion apparatus and perfused via the hepatic artery and portal vein with the oxygenated recirculating blood-based perfusate (2 liters) as described above at 36-37° C. During this initial perfusion, the delivery of oxygen to the perfusate is adjusted such that the $PO_2$ concentration in the effluent from the vena cava is sufficient to allow normal bile production. The core temperature of the liver is allowed to rise to 37° C. and when perfusate flow and pressure are near normal (hepatic artery 200-300 ml/min.;

portal vein 600-800 ml/min.), the perfusion is switched to fresh perfusate (2 liters). Perfusion is continued for approximately 15 minutes and only viable organs, in terms of perfusate flow and pressure and continuous bile production, are dosed with test compound, i.e., [$^{14}$C] acetaminophen (2-5 M in 0.5 ml DMSO).

Dosing and Sample Collection

Each dosing solution is taken up into a pre-weighed syringe with an attached cannula and the whole reweighed. The contents of the syringe are expelled as a pulse dose into the perfusate. The dosing syringe and cannula are reweighed after dosing and washed with known volumes of water/methanol. The syringe/cannula washings are assayed for radioactivity or cold compound and the dose administered calculated by subtracting the syringe washings from the total amount of radioactivity or compound taken up into the syringe/cannula.

Before and after dosing the following samples are collected:

Perfusate (10 ml): −15, 0, 5, 15, 30, 45, 60, 120, 180, 240 and 300 minutes

−15-0, 0-15, 15-30, 30-45, 45-60, 60-120, 120-240 and 240-360 minutes

Tissue biopsies: Pre-dose and after 6 hours perfusion

At the end of perfusion, the entire residual perfusate is collected and the volumes recorded. The apparatus is washed thoroughly with (a) 0.9% NaCl, (b) water, and (c) water/ethanol (1:1) mixture and the volumes of each wash solution recorded.

Sample Processing

Perfusates:

Of the 10 ml fractions collected at each time point, 2 ml are removed, of which 0.2 ml are used for blood chemistry and the remainder frozen in liquid nitrogen and stored at approximately −70° C. The remainder of each fraction (8 ml) is then centrifuged, the plasma removed, divided into 3 equal aliquots and cell pellets and plasmas flash frozen in liquid nitrogen and stored at approximately −80° C.

Bile:

Bile is collected in weighed tubes and the weight/volume of each sample recorded. Each bile sample is divided into 3 equal volumes, flash frozen in liquid nitrogen and stored at approximately −70° C.

Apparatus Washings:

After recording the volume, an aliquot of ~20 ml of each washing solution is frozen at approximately −20° C. for subsequent analysis of total radioactivity.

Tissue Biopsies:

Pre-dose biopsies (50-100 mg) are taken from both poles (n=2 from each). Two are immediately fixed in formalin and stored in a refrigerator at 4-8° C. and two are flash frozen in liquid nitrogen at the point of collection and stored in liquid nitrogen until analyzed. After 6 hours of perfusion, biopsies are taken from both poles of each major lobe and again half are fixed in formalin and half flash frozen and stored in liquid nitrogen. In addition, after 6 hours of perfusion, large wedges (~20 g) are taken from each lobe and flash frozen in liquid nitrogen for subsequent analysis of covalent binding to liver proteins.

Liver Homogenates:

After perfusion, the remainder of the liver is frozen at approximately −20° C. for subsequent homogenization and measurement of radioactive content.

Analysis

Quantitative Radiochemical Analysis and Mass Balance

Perfusate, bile and liver homogenates and the apparatus washings are analyzed for total radioactivity using combustion/scintillation counting or direct liquid scintillation techniques. All samples are analyzed in triplicate. Known weights (typically 0.1-0.2 g) of blood perfusate, plasma, liver homogenates, bile (20-50 mg) and apparatus washings are dispensed in individual paper cones and combusted for 1 minute using a Packard Oxidiser. The $^{14}$CO$_2$ produced is mixed with 8 ml of Zintox-1 absorber followed by 8 ml of Zintox-X scintillant and the samples counted using an auto-calibrated Packard 2100TR scintillation counter and quench curve for $^{14}$CO$_2$ in Zintox-1/Zintox-X. Each sample is counted for a minimum of 5 minutes (2% Sigma). The efficiency of burning (acceptance minimum 95%) is determined by burning $^{14}$C-toluene standards containing known amounts of radioactivity with each run of samples and correction made therefor. Dosing solutions (after dilution) and syringe washings are counted directly. Known weights (up to 0.5 g) of each sample are dispensed into individual tarred vials containing 2 ml of Ultima Gold XR, reweighed, thoroughly mixed by vortex and counted using the auto-calibrated Packard 2100TR scintillation counter and quench curve for $^{14}$C in Ultima Gold XR scintillant. Each sample is counted for a minimum of 5 minutes (2% Sigma).

The limit of detection is twice the dpm value for the appropriate blank or pre-dose sample and the limit of quantification is three times. The radioactivity in each sample is expressed as dpm/g sample and by multiplying the radioactive concentration by the total mass of sample, the total radioactivity associated with blood perfusate, liver and bile can be calculated and a full radiochemical balance determined. By comparing the radioactivity per gram of blood perfusate and per gram of plasma and correcting for packed cell volume, the distribution of isotope between cells and plasma with time is determined.

Example 3—Effect of the Potential Hepatotoxins on Cytochrome P450 Catalyzed Oxidation/Drug Metabolism To assess the effects of hepatotoxins on liver functions, livers are perfused with a compound, such as acetaminophen as disclosed in Example 1, for about three hours. Thereafter, one of the following cytochrome P450 substrates is added to the perfusate—phenacetin (1A$_2$), tolbutamide (2C$_9$), S-mephenytoin (2C$_{19}$), dextromethorphan (2D$_6$), chlorozoxazone (2E$_1$) or methadone (3A$_4$). After dosing, samples of perfusate and bile are collected every 30 minutes for a further 2 hours. All perfusate samples are centrifuged and the supernatants and the bile frozen at −80° C. until analyzed for dosed compounds and their metabolites. In addition, biopsy samples are assayed for genotype and phenotype of cytochrome P450 isoforms.

Analysis

Continuous measurements of perfusion pressures and flow rates are taken throughout the perfusion. In addition to blood chemistry and biochemistry (pH, PCO$_2$/PO$_2$, Na$^+$, K$^+$, Cl$^-$, Ca$^{++}$, glucose, lactate and liver enzymes), other specific markers of liver damage are quantified in the collected samples of perfusate, bile and tissue to determine the nature and the extent of liver damage. Quantification of the metabolites produced from the various cytochrome P450 substrates in the presence and absence of new chemical entities allows assessment of whether the metabolites are inhibitors or inducers and what the consequences of their activities might be to the benefit/risk ratio of potential pharmaceuticals.

| Cytochrome P450 Enzyme | Substrate | Reaction |
|---|---|---|
| CYP1A2 | Phenacetin (CH₃CH₂O—C₆H₄—NHCOCH₃) | O-deethylation |
| CYP2C9 | Tolbutamide (CH₃CH₂CH₂CH₂NH—C(=O)—NH—S(=O)₂—C₆H₄—CH₃) | 4'-hydroxylation |
| CYP2C19 | S-Mephenytoin | 4'-hydroxylation |
| CYP2D6 | Dextromethorphan | O-demethylation |
| CYP2E1 | Chlorzoxazone | 6-hydroxylation |
| CYP3A4 | Methadone | N-demethylation |

Example 4—Ex Vivo Comparison to Animal Model Study Results

The methods for using livers ex vivo for assessing toxicity provide an ethical opportunity to compare the results obtained in test animals to the results obtained in isolated human organs for compounds predicted to have hepatotoxin activity in animal model studies.

In this example, plasma clearance of compounds presumed to be removed from blood by liver, further presumably by metabolism, is studied. In some instances, this presumption is not fully supported by data such as where the $CL_{int}$ in microsomes and hepatocytes is low. These recognized shortcomings of conventional toxicity testing systems and methodologies are addressed using ex vivo livers as follows.

As set forth above, the test compound is delivered via the perfusate at physiological flow rates to a stable functional organ with normal biliary excretory processes, but without the competition from other organs. Hepatic clearance of the test compound ("compound X") at a blood concentration of μm/l and at a range of concentrations is performed using substantially the protocol set forth above in Examples 1 and 2.

In these studies, male Sprague-Dawley rats (Crl:CD® (SD) IGS BR; Charles River U.K. Ltd., Margate, Kent U.K.) are used. Rats are housed in groups of 2 or 3 (depending on size) in sawdust-lined polypropylene cases and in a single dedicated room. The holding room is maintained at a temperature of 22±4° C., with a humidity range of 40-80%, and is exposed to 12 hours fluorescent lighting (08.00-20.00 hours) followed by 12 hours darkness (20.00-08.00 hours) per day. Water is available ad libitum throughout the study. Rat and mouse Diet No. 1 (Special Diets Services Limited, Witham, Essex) is provided throughout the study. It is considered improbable that any substance absorbed from the diet or water interferes with this study.

Preparation of Perfusate

Blood (~230 ml) is collected from the dorsal aorta of donor rats under isoflurane anaesthesia into a glass container primed with a solution of lithium heparin (product code H-0878, Sigma Chemical Company, Dorset, U.K., 2,300 units in 0.46 ml of water). Glucose (2 mg/ml) and lithium heparin (to achieve 50 N.I.H units/ml blood) is added to the blood, which is then stored at room temperature until commencement of surgery, when approximately 185 ml will be added to a perfusion apparatus. The blood is oxygenated and recirculated at 37° C. prior to use. An aliquot (5 ml) of the surplus blood (~45 ml) is retained to provide matrix blanks for liquid scintillation counting and the remainder centrifuged at ~4,500×g for 10 minutes at 4° C. The plasma supernatant is removed and retained in appropriate containers for use as matrix blanks for combustion/liquid scintillation counting (~2.5 ml) and for the preparation of the standard curve (approx. 15 ml).

Rat liver donors (one per experiment) are anaesthetized with isoflurane followed by an intravenous injection of lithium heparin (4,000 N.I.H. units/kg). A mid-line abdominal incision is made and the common bile duct cannulated, toward the liver, with polyethylene tubing for the collection of bile throughout the perfusion period. The portal vein and the superior vena cava are cannulated and the liver cleared of blood with Krebs-Ringer bicarbonate buffer, pH 7.45, at 37° C. via the portal vein cannula. The liver is excised from the abdominal cavity and attached to a purpose-built perfusion apparatus. The organ is perfused with oxygenated perfusate at a flow rate of approximately 15-20 ml/min. and at a pressure of approximately 10-12 cms of water, and bile is collected continuously into pre-weighed vessels. Each liver is allowed an equilibration period (typically 20 minutes) after which the suitability of the preparation for experimental use is assessed. Only satisfactory preparations are dosed. Physiological parameters such as bile flow, temperature, flow rate and liver appearance are recorded throughout the perfusion period. Glucose (300 mg) is added to the perfusate at 90 minutes post-dose.

Administration of Compound X

Compound X dosing solution (X ml/180 ml of blood perfusate) is taken up into a pre-weighed syringe with attached polypropylene cannula and the whole weighed. The contents of the syringe are then expelled as a pulse dose into the perfusate. The dosing syringe and cannula are then reweighed after dosing and rinsed with known volumes of water/methanol. The syringe/cannula washings are assayed for radioactivity/parent compound and the dose administered calculated by subtracting the syringe washings from the total radioactivity/weight of compound taken up into the syringe/cannula.

In a first experiment, the target blood perfusate concentration is µm/l (x MBq/ml). Triplicate pre- and post-dose samples (typically 0.05 g) of dosing solution are flash frozen at the point of collection for subsequent radiochemical purity analysis using HPLC with on-line radiodetection and possible analysis by the sponsor. Residual compound X dosing solution is retained if needed for comparison.

Sample Collection, Processing and Storage

A pre-dose sample of blood perfusate (~5 ml) and the entire bile are collected prior to dosing. The timing of all subsequent collections of bile and plasma is taken from the time at which the pulse dose of compound X is administered. All samples are collected in pre-weighed tubes and reweighed following sampling in order that the samples mass is determined. The tubes are placed on ice following collection to minimize evaporation and metabolite degradation and are processed as quickly as possible. The following samples are collected from the perfused rat liver preparation post-dose:

| | |
|---|---|
| Blood perfusate (5 ml)/plasma: | 5 minutes, 10 minutes, 15 minutes, 30 minutes, 45 minutes, 1 hour, 2 hours and 3 hours |
| Bile: | 0-15 minutes, 15-30 minutes, 30-60 minutes, 1-1.5 hours, 1.5-2.0 hours, 2.0-2.5 hours and 2.5-3 hours |
| Liver: | 3 hours |

A portion of each blood perfusate sample (1 ml) is retained whole and the remainder centrifuged and the plasma (~2 ml) harvested and divided into 4×0.5 ml aliquots. The blood cell pellet is retained. The bile is divided into equal aliquots. The liver is homogenized (~20% w/v) in water on ice and the homogenate retained as 3 aliquots. The residual blood in the apparatus is taken with a volume (10 ml), retained whole and the remainder centrifuged and the plasma harvested and retained in multiple aliquots. The apparatus is thereafter rinsed with known volumes of water followed by methanol and the washings retained.

All samples are placed in a −80° C. freezer as soon as possible following collection.

Analysis

Quantitative Radiochemical Analysis

Blood, plasma, bile, liver homogenate and the apparatus washings are analyzed for total radioactivity using combustion/liquid scintillation counting or direct liquid scintillation techniques, with all samples being analyzed in triplicate. Known weights (typically 0.1 g-0.2 g) of blood perfusate and liver homogenates are dispensed in individual paper cones and combusted for 1 minute using a Packard Oxidiser 307. The $^{14}CO_2$ produced is then mixed with 8 ml of Zintox-1 absorber followed by 8 ml of Zintox-X scintillant and the samples counted using an auto-calibrated Packard 2100TR scintillation counter and quench curve for $^{14}CO_2$ in Zintox-1/Zintol-X. Each sample is counted for a minimum of 5 minutes (2% Sigma). The efficiency of burning (acceptance minimum 95%) is determined by burning $^{14}C$-toluene standards containing known amounts of radioactivity with each run of samples and corrected thereby. Dosing solutions (after dilution), syringe washings, plasma, bile and perfusion apparatus washings are counted directly. Known weights (up to 0.5 g) of each sample are dispensed in individual tarred vials containing 2 ml of Ultima Gold XR, reweighed, thoroughly mixed by vortex and counted using the auto-calibrated Packard 2100TR scintillation counter and quench curve for $^{14}C$ in Ultima Gold XR scintillant. Each sample is counted for a minimum of 5 minutes (2% Sigma).

The limit of detection of the data is twice the dpm value for the appropriate blank or pre-dose sample and the limit of quantification is three times. The radioactivity in each sample is expressed as dpm/g sample and by multiplying the radioactive concentration by the total mass of sample, the total radioactivity associated with blood perfusate (samples, residual and apparatus wash), liver homogenate and bile can be calculated and a full radiochemical balance determined. The decrease in blood and plasma radioactivity with time can be plotted and by comparing the radioactivity per gram of blood perfusate and per gram of plasma and correcting for packed cell volume of the former, the distribution of radioactivity between cells and plasma with time determined.

Hepatic Clearance of Compound X

The clearance of parent drug is calculated from concentration data and compared with clearance of total radioactivity, described above, to determine the role of metabolism (if any) in the clearance process, using one of the following:

Method 1: Clearance (ml/min.) is determined by dividing the total amount of compound (µM/min.) lost from the plasma between 2 time points, e.g., 10-30 minutes by the plasma concentration (µM equivalents per ml, assuming density of plasma to be 1.0) at the mid point, i.e., 20 minutes.

Method 2: In recirculating systems the hepatic clearance ($CL_H$) is estimated from the dose of compound administered to the perfusate and the total area under the compound versus time curve (AUC), i.e., $CL_H$=dose/AUC. The AUC can be calculated by the trapezoidal method and extrapolated to infinite time. Accurate estimation of the AUC requires a concentration time profile of a minimum of 2-3 half-lives of the compound. Hepatic extraction ($E_H$) is calculated indirectly from $CL_H$ using the following equation $E_H=CL_H/Q$, where Q is the flow rate.

Using either of these methods, the hepatic clearance rate of the test compound can be determined.

Example 5—Drug Delivery to Ex Vivo Human and Animal Intestine

Oral bioavailability depends on a number of factors involved in formulations of orally-administered drugs. One novel class of bactericidal compounds, termed DRIs, inhibits protein synthesis using a different mode of action than other known translation inhibitors. However, a key deficit of DRIs is poor oral bioavailability, at least in preclinical species, which may be the result of its high molecular weight and poor intestinal permeability because blood clearance tends to be low, while solubility is relatively high.

In this study, DRI absorption across perfused rat intestine (a species where bioavailability is low) is compared with absorption by human intestine (for which, as the target species, bioavailability has been well-characterized).

Prior to perfused rat and human intestine experiments, each drug candidate is assessed for: (a) stability in two perfusates (one for rat and a separate perfusate for human intestine); and (b) quantitative distribution between erythrocytes and plasma at 37° C. in both perfusates. This ensures that in all intestine perfusion experiments, the amount of each compound appearing in the perfusate plasma accurately measures the amount of compound transported from the intestinal lumen into the circulation.

Absorption from Rat and Human Intestine

After a stabilization period, each isolated vascular perfused segment of rat or human intestine is dosed into the lumen with equimolar amounts of one or more DRIs (preferably in the same formulation). Aliquots of perfusate are withdrawn at timed intervals and the perfusate plasma assayed for test compounds. From the known concentration of each compound in perfusate and the volume of perfusate, the percent of the dose for each compound absorbed with time is determined.

Stability Studies in Perfusate

Prior to the intestine perfusion studies, the stability of the test compounds in the heparinized blood perfusate is determined in: (a) the rat blood based perfusate; and (b) the human erythrocyte based perfusate. Cassettes of compounds (n=1-5 per cassette) are added to both recirculating oxygenated perfusates (150 ml) at pH 7.4 and 37° C. Aliquots (3-5 ml) of the perfusate are removed at 0, 1, 2 and 3 hours post-dosing. Each sample is divided into 2 equal portions, with one half being centrifuged, the plasma removed and frozen at approximately −70° C. The remaining half of each perfusate aliquot is frozen at approximately −70° C. Samples of perfusate and perfusate plasma are analyzed for parent drug, and only compounds found to be sufficiently stable in the recirculating perfusates over 3 hours are tested for absorption rates in the perfused human and rat intestine preparations.

Absorption of Test Compounds from the Lumen of Perfused Rat Intestine

Preparation of Perfusate

On the day of perfusion, blood is collected from the dorsal aorta of donor rats (4 per perfusion) under isoflurane anesthesia into heparinized (1,000 N.I.H.) containers. The blood is diluted with Krebs-Ringer bicarbonate buffer, pH 7.4, containing 6% (w/v) bovine serum albumin (factor V) and glucose (1 mg/ml) with a final perfusate volume of 150 ml. The blood dilution factor is standardized to be the same for each perfusion experiment, wherein donor blood typically comprises about 20% of the total perfusate volume. The pH of the perfusate is monitored and adjusted to 7.4 by the addition of 0.75 M $NaHCO_3$. The perfusate is transferred to the perfusion apparatus for equilibration at 37° C. and oxygenation prior to use.

Intestine Surgery and Perfusion Conditions

Prior to surgery, rats are given free access to food and water. For each intestine preparation, the donor rat is anaesthetized with isoflurane followed by an intravenous injection of sodium pentabarbitone (approximately 60 mg/kg body weight). The trachea is cannulated with polyethylene tubing to facilitate respiration during anesthesia and the right jugular vein cannulated with polyethylene tubing for the administration of additional sodium pentabarbitone as required. A mid-line abdominal incision is made and the intestines exposed. The vascular supply to the stomach, spleen, pancreas and rectum is ligated with suture and the intestine occluded immediately above the rectum. In addition, the common bile duct is ligated. Heparin (approximately 1,000 N.I.H. units) is administered via the jugular vein cannula, and then the mesenteric artery and portal vein cannulated and the vascular bed flushed free of blood with a small volume of Krebs-Ringer bicarbonate buffer, pH 7.4, at 37° C. The donor rat is euthanized with a lethal dose of sodium pentabarbitone administered via the jugular vein cannula. The intestine preparation is then transferred to the purpose-built perfusion cabinet and perfused in situ via the mesenteric artery with recirculating oxygenated perfusate (150 ml) and equilibrated at a perfusion pressure of 50-80 mmHg and flow of approximately 10 ml perfusate/min.

At the extreme proximal end of the isolated segment of the ileum, a small incision is made in the intestinal wall and a cannula inserted into the lumen and secured with surgical thread. A fixed volume of test compound (0.5-1.0 ml) is then administered as a pulse dose, the inlet cannula removed and the opening in the intestinal wall sealed with surgical thread. Pre- and post-dosing perfusate samples are collected, processed and stored as described below.

Absorption of Test Compounds from the Lumen of Perfused Human Intestine

Isolated segments (approximately 30 cm) of human intestine, immediately below the entry of the bile duct, are perfused via the mesenteric artery (or a branch thereof) with a perfusate comprised of matched human erythrocytes (20-25% v/v) suspended in RS1 containing 6% w/v human albumin at 37° C., pH 7.4 and 60-80 mmHg pressure. Test compounds together with four positive/negative controls, are co-administered in the same formulation into the lumen of the intestinal segment. The segment is perfused for a further 2 hours and 3-5 ml aliquots of the perfusate removed at the following times: pre-dose, and 5, 10, 15, 30 and 45 minutes, 1, 1.5 and 2 hours. Approximately half of each aliquot sample is frozen at −70° C. and the remainder of each aliquot is centrifuged, the plasma removed and frozen at −70° C.

At termination, the lumen of the intestinal segment is washed with water and the washings retained for analysis. The tissue is homogenized and frozen for subsequent optional analysis of dosed compounds.

Analysis

After appropriate extractions of perfusate and/or perfusate plasma, each sample is analyzed for test compounds and positive/negative controls (n=4) using appropriate analytical methods. For each experiment, the rate of transfer of test compounds from the intestinal lumen into blood is determined and normalized against passively transported controls.

Example 6—Partitioning/Clearance of Drugs and Metabolites in Bile and Perfusate These experiments are directed at assaying drugs perfused through livers ex vivo for the relative distribution of the drug and metabolites thereof between the perfusate (representing the bloodstream in vivo) and bile (representing the major pathway for drug and metabolites to be eliminated from the body in vivo). These experiments thus study hepatic clearance, metabolism and distribution of metabolites between bile and perfusate following dosing of radiolabeled test compounds to isolated perfused human livers.

The perfusate, perfusate plasma, bile and liver homogenates are assayed quantitatively by combustion followed by liquid scintillation counting. The distribution of parent drug and metabolite(s) between perfusate plasma and bile is determined, inter alia, by HPLC of suitable extracts with online radiodetection.

Hypothermic Perfusates

As soon as possible after harvest, livers are attached to a perfusion system such as LifePort® (as disclosed in co-owned U.S. Pat. No. 6,673,594, incorporated by reference) and perfused with RS1 buffer pH 7.4 at 17° C.

Perfusion Conditions

Hypothermic perfusion (17° C.) of the donor liver delivered via the hepatic artery and portal vein is stopped immediately prior to beginning the experiments described herein.

Bile samples and extracts of plasma and liver tissue are analyzed by HPLC with online radiodetection. The proportions of test compound versus radiolabeled metabolite(s) can be determined by integrating peak areas, and this together the total radioactivity in each sample is used to quantify each metabolite.

Example 7—Ex Vivo Assays of Individual Differences in Reactions to Drugs

As described above, in drug development, the appearance of either new metabolites or vastly different amounts of particular metabolites in first studies in humans can lead to a considerable amount of extra work, resources and time lost. Therefore a system designed to provide early notification of human drug metabolism would be of long-term value to drug development.

The primary purpose of these experiments is to determine the nature and extent of metabolism of $^{14}$C-labeled drug in the isolated perfused human liver, the subsequent partitioning of metabolites between blood and bile and the mass-balance of radioactivity.

Preparation of Perfusates

Livers ex vivo are perfused at hypothermic temperatures using Lactated Ringer's Injection USP (Baxter) and RS1 at 4-8° C. For normothermic perfusion, outdated, matched human erythrocytes are washed (four times) in an equal volume of lactated Ringer's with intermediate centrifugation. For the final wash the packed cells are re-suspended in RS1 buffer (pH 7.4), centrifuged and as much as possible of the supernatant carefully aspirated taking as much as possible of the buffy coat using a hand held pipette. Finally, the washed packed cells are resuspended in RS1 buffer (pH 7.4) containing N-acetyl cysteine (25 mg/l), ATP (20 mg/l), heparin (1500 units/l) and human albumin (4% w/v), whereby the packed cell volume is approximately 15-20% (v/v) of the total perfusate volume. The perfusate is passed through a Pall leukocyte filter to remove any remaining cells, the pH adjusted, if necessary to 7.4, and stored at room temperature until added to the perfusion apparatus (2 liters per perfusion). An aliquot of the surplus perfusate (50 ml) is centrifuged (~1500×g for 10 minutes at 4° C.) to separate the plasma and blood cells. This plasma is frozen at ~70° C. and kept for possible use in the analysis.

Perfusion Procedure

Livers (<30 hours CIT) are removed from hypothermic storage, weighed, and the following vessels cannulated: hepatic artery, portal vein and bile ducts from the liver and gall bladder. To remove residual storage solution, both the artery and vein are flushed with 500 ml of Ringers followed by 500 ml of RS1. The erythrocyte-based perfusate (2 liters) is heated by being placed in a water bath (at 37° C.) and the apparatus primed. The liver is attached and perfused with target flows of 300-400 ml/min. (arterial) and 600-800 ml/min. (venous). When the core temperature of the liver is >35° C. and bile is flowing, the preparation is dosed with $^{14}$C-labeled drugs, as a pulse dose into the perfusate.

Dosing and Sample Collection

Once the preparation is stable with respect to perfusate flow and pressure, pre-dose control samples of perfusate and bile are taken and a $^{14}$C-labeled drug (35 mg) added to the recirculating perfusate as described above.

Each dosing solution is taken up into a pre-weighed syringe with an attached cannula and the whole re-weighed. The contents of the syringe are expelled as a pulse dose into the perfusate. The dosing syringe and cannula are reweighed after dosing and washed with known volumes of water/methanol. The syringe/cannula washings are assayed for radioactivity and the dose administered calculated by subtracting the syringe washings from the total amount of radioactivity taken up into the syringe/cannula.

The following samples are collected over a 6 hour perfusion period:

| | |
|---|---|
| Perfusate (6 ml): | pre-dose and 5, 10, 15 and 30 minutes, 1, 1.5, 2, 3, 4, 5 and 6 hours post-dose |
| Bile: | pre-dose and 0-0.5, 0.5-1, 1-1.5, 1.5-2, 2-2.5, 2.5-3, 3-3.5, 3.5-4, 4-4.5, 4.5-5, 5-5.5 and 5.5-6 hours post-dose |

At 1.5, 3.0 and 4.5 hours, a mixture of a positive control (phenolphthalein glucuronide) and a negative control ($^3$H-mannitol) for biliary elimination is added to the perfusate.

The perfusate aliquots are centrifuged and each plasma sample divided into 5 equal aliquots, flash frozen at the point of collection and stored at approximately −70° C. After recording the weight, each bile sample is divided into 3 equal aliquots, flash frozen and stored at approximately −70° C.

In all liver perfusion experiments small biopsies are removed from upper and lower poles before and after normothermic perfusion and the sites recorded with a digital camera. Each biopsy is flash frozen in liquid nitrogen at the point of collection and stored therein until required.

All patents, patent applications, scientific article and other sources and references cited herein are explicitly incorporated by reference herein for the full extent of their teachings as if set forth in their entirety explicitly in this application.

It should be understood that the foregoing disclosure emphasizes certain specific embodiments of the invention

What we claim is:

1. A method of developing a pharmaceutical product, comprising:
   passing a perfusate comprising at least one substance to be evaluated through at least one metabolically active human organ selected from the group consisting of liver, lung, kidney, heart, pancreas, testes, thymus, adrenal gland, and lymph nodes that has been permanently removed from its origin and is unsuitable for transplantation, wherein the perfusate is delivered via a perfusion apparatus;
   collecting data derived from the perfused organ and storing the data in a computer-readable medium, wherein the data is evaluated via a computer analysis to identify similarities or patterns; including at least one of the following: substance absorption by the organ, substance bioavailability, substance toxicity, substance interaction with at least one other substance, substance therapeutic effect, substance metabolite generation or liver clearance of the substance;
   quantifying a functional state of the at least one metabolically active human organ selected from the group consisting of liver, lung, kidney, heart, pancreas, testes, thymus, adrenal gland, and lymph nodes by including positive and negative controls in a perfusate that does not contain the at least one substance to be evaluated that is passed through the least one metabolically active human organ after perfusing the at least one metabolically active human organ with the perfusate that contains the at least one substance to be evaluated, wherein the at least one metabolically active human organ selected from the group consisting of liver, lung, kidney, heart, pancreas, testes, thymus, adrenal gland, and lymph nodes acts as its own control; and
   continuing or terminating development of the substance into a pharmaceutical product based upon an analysis of the collected data.

2. The method of claim 1, comprising using the collected data in at least one pharmaceutical development phase selected from the group consisting of: discovery, pre-clinical, phase I, phase II, phase in and phase IV.

3. The method of claim 1, further comprising passing a second substance through the organ.

4. The method of claim 1, wherein the organ is diseased.

5. The method of claim 1, wherein the passing comprises perfusing the organ with a first fluid that does not contain the substance, followed by perfusing the organ with a second fluid that contains the substance;
   wherein
      the first fluid that does not contain the substance is delivered via a perfusion apparatus, and
      the second fluid that contains the substance is delivered via a perfusion apparatus.

6. The method of claim 1, wherein the data are collected by collecting at least one perfusate sample, taking at least one biopsy from the organ, and collecting at least one bodily fluid sample or a mixture thereof.

7. The method of claim 6, wherein the data are collected by taking a biopsy from the organ.

8. The method of claim 6, wherein the organ is selected from the group consisting of: liver, kidney, lung, pancreas and heart.

9. The method of claim 8, wherein the organ is a liver, and is perfused with a perfusate delivered via a perfusion apparatus, the perfusate comprising at least one of the following: 37-150 mg/l N-acetylcysteine, 5-20 mg/l ATP, 12-50 µM dibutylcyclic AMP, 1-4 µg superoxide dismutase (in 5% acid), 50-200 µM glycocholic acid, or 25-100 µM glycochenodeoxycholic acid.

10. The method of claim 9, wherein the perfusate further comprises 50-200 µg $^3$H-mannitol.

11. The method of claim 8, wherein the data are collected by collecting a bodily fluid sample and the bodily fluid sample comprises bile or bile duct excretions.

12. The method of claim 8, wherein the organ is a kidney, and is perfused with a perfusate delivered via a perfusion apparatus, the perfusate comprising 1-5 µl/l noradrenaline and/or 1-4.5 ml/l dexamethasone.

13. The method of claim 8, wherein the data are collected by collecting a bodily fluid sample and the bodily fluid sample comprises urine or ureter filtrate.

14. The method of claim 8, wherein the organ is an organ selected from the group consisting of liver, kidney, lung, pancreas and heart.

15. The method of 14, wherein
   the organ is a liver,
   the at least one substance and the positive and negative controls are delivered via matched blood-based perfusate at physiological flow rates to the liver, and
   the step of collecting data derived from the perfused organ comprises:
      determining the nature and extent of uptake, metabolism and clearance of the at least one substance,
      assessing biliary elimination and mass-balance of the at least one substance, and
      preforming measurements of the subsequent partitioning of metabolites between blood and bile.

16. The method of claim 8, wherein the data are collected by collecting a bodily fluid sample.

17. The method of claim 8, wherein the data are collected by collecting a bodily fluid sample and the bodily fluid sample comprises pancreatic excretions.

18. The method of claim 1, wherein the organ is perfused through a perfusate comprising type-matched human red blood cells.

19. The method of claim 1, wherein the data are collected using microdialysis.

20. The method of claim 1, wherein the data are collected via conducting an MRI, CT or PET.

21. The method of claim 1, wherein the data are collected via spectroscopic testing selected from the group consisting of light, infrared and ultraviolet spectroscopic techniques.

22. The method of claim 1, wherein the data are collected via solid state tissue probe testing, which comprises using at least one pH probe.

23. The method of claim 1, wherein the organ is a heart, and the data are collected via conducting an electrocardiogram.

24. The method of claim 1, wherein
   the metabolically active human organ is a lung, and
   the step of collecting data derived from the perfused organ comprises:
      assessing inhaled drug performance by quantitating ventilatory function, drug preparation stability, drug absorption via the airways, drug uptake from the blood, drug metabolism, clearance and retention, and extent of edema.

25. The method of claim 1, wherein
   the metabolically active human organ is a kidney, and
   the perfusate used is derived from a liver perfusion experiment in which a test compound has been perfused through a human liver.

26. The method of claim 1, wherein the metabolically active human organ is a heart, and
  the step of collecting data derived from the perfused organ comprises:
    measuring and monitoring the electrolytes levels, glucose levels, a $PO_2$ A-V difference, and a $PCO_2$ A-V difference in the perfusate.

27. The method of claim 1, wherein the metabolically active human organ is a pancreas.

28. The method of claim 1, wherein the metabolically active human organ or tissue is selected from the group consisting of thymus, adrenal gland, and lymph nodes.

\* \* \* \* \*